US012799090B2

(12) United States Patent
Parker et al.

(10) Patent No.: US 12,799,090 B2
(45) Date of Patent: Nov. 17, 2026

(54) MOTHER LIQUOR COMPOSITION GENERATED IN MCFC PROCESS

(71) Applicant: Eastman Chemical Company, Kingsport, TN (US)

(72) Inventors: Kenny Randolph Parker, Afton, TN (US); Mesfin Ejerssa Janka, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 380 days.

(21) Appl. No.: 18/560,956

(22) PCT Filed: May 12, 2022

(86) PCT No.: PCT/US2022/028900

§ 371 (c)(1),
(2) Date: Nov. 15, 2023

(87) PCT Pub. No.: WO2022/245618

PCT Pub. Date: Nov. 24, 2022

(65) Prior Publication Data

US 2024/0317698 A1 Sep. 26, 2024

Related U.S. Application Data

(60) Provisional application No. 63/201,949, filed on May 20, 2021.

(51) Int. Cl.
*C07D 307/68* (2006.01)

(52) U.S. Cl.
CPC .................................. *C07D 307/68* (2013.01)

(58) Field of Classification Search
CPC .................................................... C07D 307/68
See application file for complete search history.

(56) References Cited

U.S. PATENT DOCUMENTS

| | | | |
|---|---|---|---|
| 2,829,153 | A | 4/1958 | Vodonik |
| 2,905,707 | A | 9/1959 | Hurt |
| 3,054,776 | A | 9/1962 | Higgins |
| 3,118,843 | A | 1/1964 | Stuetzer |
| 3,385,881 | A | 5/1968 | Bachmann et al. |
| 3,577,411 | A | 5/1971 | Liechti et al. |
| 3,582,244 | A | 6/1971 | Siclari et al. |
| 3,584,039 | A | 6/1971 | Meyer |
| 3,600,137 | A | 8/1971 | Girantet et al. |
| 3,644,096 | A | 2/1972 | Lewis et al. |
| 3,689,461 | A | 9/1972 | Balint |
| 3,819,585 | A | 6/1974 | Funk et al. |
| 3,996,271 | A | 12/1976 | Yokota et al. |
| 4,110,316 | A | 8/1978 | Edging et al. |
| 4,158,738 | A | 6/1979 | Scott et al. |
| 4,230,818 | A | 10/1980 | Broughton, Jr. et al. |
| 4,235,844 | A | 11/1980 | Sterzel et al. |
| 4,289,895 | A | 9/1981 | Burkhardt et al. |
| 5,095,141 | A | 3/1992 | Schammel et al. |
| 8,772,513 | B2 | 7/2014 | Janka et al. |
| 8,796,477 | B2 | 8/2014 | Janka et al. |
| 8,846,960 | B2 | 9/2014 | Janka et al. |
| 8,865,921 | B2 | 10/2014 | Diego et al. |
| 9,156,805 | B2 | 10/2015 | Shaikh et al. |
| 9,206,149 | B2 | 12/2015 | Janka et al. |
| 9,765,045 | B2 | 9/2017 | Strensrud et al. |
| 10,344,011 | B1 | 7/2019 | Parker et al. |
| 10,421,736 | B2 | 9/2019 | Fontenot et al. |
| 10,526,301 | B1 | 1/2020 | Fontenot et al. |
| 10,544,118 | B2 | 1/2020 | Janka et al. |
| 10,882,032 | B2 | 1/2021 | Fontenot et al. |
| 10,941,245 | B2 | 3/2021 | Janka et al. |
| 11,236,199 | B2 | 2/2022 | Janka |
| 11,440,895 | B2 | 9/2022 | Janka et al. |
| 11,655,334 | B2 | 5/2023 | Janka et al. |
| 11,787,774 | B2 | 10/2023 | Janka |
| 2005/0208582 | A1 | 9/2005 | Ohi et al. |
| 2006/0205977 | A1 | 9/2006 | Sumner et al. |
| 2010/0210867 | A1 | 8/2010 | Bustamante et al. |
| 2012/0059178 | A1 | 3/2012 | Sanborn |
| 2012/0283452 | A1 | 11/2012 | Diego et al. |
| 2012/0302768 | A1 | 11/2012 | Janka et al. |
| 2012/0302769 | A1 | 11/2012 | Janka et al. |
| 2012/0302770 | A1 | 11/2012 | Janka et al. |
| 2012/0302771 | A1 | 11/2012 | Janka et al. |
| 2012/0302772 | A1 | 11/2012 | Shaikh et al. |

(Continued)

FOREIGN PATENT DOCUMENTS

| | | | |
|---|---|---|---|
| CN | 111153876 | A | 5/2020 |
| DE | 1146055 | B | 3/1963 |

(Continued)

OTHER PUBLICATIONS

Co-pending application U.S. Appl. No. 16/430,628, filed Jun. 4, 2019, Janka.
USPTO Office Action dated Jun. 11, 2020 received in co-pending U.S. Appl. No. 16/430,628 (U.S. Publication 2019-0389822).
USPTO Notice of Allowance dated Dec. 10, 2020 received in co-pending U.S. Appl. No. 16/430,628.
Co-pending application U.S. Appl. No. 16/430,687, filed Jun. 4, 2019, Janka.
USPTO Office Action dated Mar. 9, 2020 received in co-pending U.S. Appl. No. 16/430,687 (U.S. Publication 2019-0389823).
USPTO Office Action dated Oct. 21, 2020 received in co-pending U.S. Appl. No. 16/430,687 (U.S. Publication 2019-0389823).
USPTO Office Action dated May 3, 2021 received in co-pending U.S. Appl. No. 16/460,687.

(Continued)

*Primary Examiner* — Timothy R Rozof
(74) *Attorney, Agent, or Firm* — Steven A. Owen

(57) ABSTRACT

Disclosed herein is a method to make 5-(alkoxycarbonyl) furan-2-carboxylic acids (ACFC) from feedstocks comprised of furoates. When a feedstock comprised of methyl 5-methylfuran-2-carboxylate (MMFC) is used a product comprised of (5-methoxycarbonyl)furan-2-carboxylic acid (MCFC) is obtained in high yield.

20 Claims, 2 Drawing Sheets

(56) References Cited

U.S. PATENT DOCUMENTS

| | | | |
|---|---|---|---|
| 2012/0302773 A1 | 11/2012 | Janka et al. | |
| 2013/0345447 A1 | 12/2013 | Shaikh et al. | |
| 2013/0345448 A1 | 12/2013 | Shaikh et al. | |
| 2014/0066639 A1 | 3/2014 | Janka et al. | |
| 2014/0128623 A1 | 5/2014 | Janka et al. | |
| 2014/0128624 A1 | 5/2014 | Janka et al. | |
| 2014/0235880 A1 | 8/2014 | Shaikh et al. | |
| 2015/0315166 A1 | 11/2015 | Stensrud et al. | |
| 2016/0024039 A1 | 1/2016 | Mazoyer et al. | |
| 2016/0207898 A1 | 7/2016 | Singh et al. | |
| 2016/0221980 A1 | 8/2016 | Parker et al. | |
| 2017/0313670 A1 | 11/2017 | De Sousa Dias et al. | |
| 2018/0155306 A1 | 6/2018 | McKay et al. | |
| 2019/0023677 A1 | 1/2019 | Fontenot et al. | |
| 2019/0031634 A1 | 1/2019 | Metkar et al. | |
| 2019/0389820 A1 | 12/2019 | Janka | |
| 2019/0389821 A1 | 12/2019 | Janka | |
| 2019/0389822 A1* | 12/2019 | Janka | B01J 23/75 |
| 2019/0389823 A1 | 12/2019 | Janka | |
| 2019/0389824 A1 | 12/2019 | Janka | |
| 2019/0389825 A1 | 12/2019 | Janka | |
| 2019/0389846 A1 | 12/2019 | Janka | |
| 2019/0390004 A1 | 12/2019 | Janka | |
| 2020/0123119 A1 | 4/2020 | Fontenot et al. | |

FOREIGN PATENT DOCUMENTS

| | | |
|---|---|---|
| EP | 2784069 A1 | 10/2014 |
| WO | WO 98/10007 A1 | 3/1998 |
| WO | WO 2010/132740 A2 | 11/2010 |
| WO | WO 2011/043660 A2 | 4/2011 |
| WO | WO 2011/043661 A1 | 4/2011 |
| WO | WO 2012-161967 A1 | 11/2012 |
| WO | WO 2012/161970 A2 | 11/2012 |
| WO | WO 2015/171704 A1 | 11/2015 |
| WO | WO 2016/068712 A1 | 5/2016 |
| WO | WO 2016-126975 A1 | 8/2016 |
| WO | WO 2016-195499 A1 | 12/2016 |
| WO | WO 2016-195500 A1 | 12/2016 |
| WO | WO 2016-202858 A1 | 12/2016 |
| WO | WO 2017-019441 A1 | 2/2017 |
| WO | WO 2017/076947 A1 | 5/2017 |
| WO | WO 2019/170204 A1 | 9/2019 |
| WO | WO 2020/005607 A1 | 1/2020 |
| WO | WO 2021/045927 A1 | 3/2021 |
| WO | WO 2021/123203 A1 | 6/2021 |

OTHER PUBLICATIONS

Co-pending application U.S. Appl. No. 16/561,469, filed Sep. 5, 2019, Janka.

USPTO Office Action dated Apr. 10, 2020 received in co-pending U.S. Appl. No. 16/561,469 (U.S. Publication 2019-0389820).

USPTO Office Action dated Jan. 22, 2021 received in co-pending U.S. Appl. No. 16/561,469 (U.S. Publication 2019-0389820).

USPTO Office Action dated Sep. 28, 2021 received in co-pending U.S. Appl. No. 16/561,469.

Co-pending application U.S. Appl. No. 16/561,484, filed Sep. 5, 2019, Janka.

USPTO Office Action dated Apr. 14, 2020 received in co-pending U.S. Appl. No. 16/561,484 (U.S. Publication 2019-0389846).

USPTO Office Action dated Oct. 9, 2020 received in co-pending U.S. Appl. No. 16/561,484 (U.S. Publication 2019-0389846).

USPTO Office Action dated Apr. 16, 2021 received in co-pending U.S. Appl. No. 16/561,484 (U.S. Publication 2019-0389846).

Co-pending application U.S. Appl. No. 16/430,694, filed Jun. 4, 2019, Janka.

USPTO Office Action dated May 18, 2020 received in co-pending U.S. Appl. No. 16/430,694 (U.S. Publication 2019-0389824).

USPTO Office Action dated Sep. 8, 2020 received in co-pending U.S. Appl. No. 16/430,694 (U.S. Publication 2019-0389824).

USPTO Office Action dated Mar. 18, 2021 received in co-pending U.S. Appl. No. 16/430,694 (U.S. Publication 2019-0389824).

USPTO Office Action dated Jul. 22, 2021 received in co-pending U.S. Appl. No. 16/430,694.

UPSTO Office Action dated Dec. 9, 2021 received in co-pending U.S. Appl. No. 16/430,694.

USPTO Notice of Allowance dated May 4, 2022 received in co-pending U.S. Appl. No. 16/430,694.

Co-pending application U.S. Appl. No. 16/430,607, filed Jun. 4, 2019, Janka.

Notice of Allowance dated Nov. 20, 2019 received in co-pending U.S. Appl. No. 16/430,607(Now U.S. Pat. No. 10,544,118).

Co-pending application U.S. Appl. No. 16/430,704, filed Jun. 4, 2019, Janka.

USPTO Office Action dated Mar. 6, 2020 received in co-pending U.S. Appl. No. 16/430,704(U.S. Publication 2019-0389285).

USPTO Office Action dated Jul. 13, 2020 received in co-pending U.S. Appl. No. 16/430,704 (U.S. Publication 2019-0389825).

USPTO Office Action dated Nov. 13, 2020 received in co-pending U.S. Appl. No. 16/430,704 (U.S. Publication 2019-0389825).

USPTO Office Action dated Mar. 19, 2021 received in co-pending U.S. Appl. No. 16/430,704 (U.S. Publication 2019-0389825).

USPTO Office Action dated Jul. 28, 2021 received in co-pending U.S. Appl. No. 16/430,704.

Co-pending application U.S. Appl. No. 16/430,717, filed Jun. 4, 2019, Janka.

USPTO Office Action dated Apr. 15, 2021 received in co-pending U.S. Appl. No. 16/430,717.

USPTO Office Action dated Nov. 8, 2021 received in co-pending U.S. Appl. No. 16/430,717.

USPTO Office Action dated Mar. 10, 2022 received in co-pending U.S. Appl. No. 16/430,717.

Notice of Allowance dated Mar. 1, 2023 received in co-pending U.S. Appl. No. 16/430,717.

Co-pending application U.S. Appl. No. 17/753,399, filed Mar. 2, 2022, Janka.

USPTO Office Action dated May 9, 2023 received in co-pending U.S. Appl. No. 17/753,399.

Co-pending Application U.S. Appl. No. 18/560,961, filed Nov. 15, 2023.

Co-pending Application U.S. Appl. No. 18/560,953, filed Nov. 15, 2023.

Notification of Transmittal of The International Search Report and The Written Opinion of the International Searching Authority, or the Declaration; International Application No. PCT/US2019/037427 with a filing date of Jun. 17, 2019.

Notification of Transmittal of The International Search Report and The Written Opinion of the International Searching Authority, or the Declaration; International Application No. PCT/US2020/047716 with a filing date of Dec. 4, 2020.

Notification of Transmittal of The International Search Report and The Written Opinion of the International Searching Authority, or the Declaration; International Application No. PCT/US2022/028926 with a filing date of Sep. 13, 2022.

Notification of Transmittal of The International Search Report and The Written Opinion of the International Searching Authority, or the Declaration; International Application No. PCT/US2022/028931 with a filing date of Sep. 19, 2022.

Notification of Transmittal of The International Search Report and The Written Opinion of the International Searching Authority, or the Declaration; International Application No. PCT/US2022/028900 with a filing date of Sep. 8, 2022.

Gandini, Alessandro, et al.; "The Furan Counterpart of Poly(ethylene terephthalate): An Alternative Material Based on Renewable Resources"; Journal of Polymer Science: Part A: Polymer Chemistry, vol. 47, (2009), pp. 295-298.

Moraes, Maria De Lourdes L., et al., "Analysis of impurities in crude and highly-purified terephthalic acid by capillary electrophoresis", Journal of the Brazilian Chemical Society, 2004, vol. 15, No. 3, pp. 400-406.

Shen, Yong, et al.; "Facile preparation of bio-based polyesters from furandicarboxylic acid and long chain diols via asymmetric monomer strategy"; Green Chem., 2017, 19, 4930-4938.

(56) References Cited

OTHER PUBLICATIONS

Langolf, Sebastian, et al.; Development of Antitrypanosomal and Antiplasmodial Nonpeptidic Cysteine Inhibitors based on N-Protected-Guanidino-Furan and -Pyrrole Building Blocks; ChemMedChem, 2011, 6, pp. 1581-1586.
Schmuck, Carsten, et al.; 2-(Guanidiniocarbonyl)furans as a New Class of Potential Anion Hosts: Synthesis and First Binding Studies; European Journal of Organic Chemistry, 2006, 19, pp. 4385-4392.
Zuo, Xiaobin, et al.; Optimization of Co/Mn/Br-Catalyzed Oxidation of 5-Hydroxymethylfurfural to Enhance 2,5-Furandicarboxylic Acid Yield and Minimize Substrate Burning; ACS Sustainable Chem. Eng., 2016, vol. 4, pp. 3659-3668.
Partenheimer, Walt, et al.; "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts"; Advanced Synthetic Catal., 2001, 343, No. 1, 102-111.
Tojo, Gabriel et al.; "Oxidation of Primary Alcohols to Carboxylic Acids", Chapter 1, Springer, 2007, 17 pages.
Deng, Jin et al.; Aerobic Oxidation of Hydroxymethylfurfural and Furfural by Using Heterogeneous $Co_xO_y$—N@C Catalysts; Chemsuschem, 2014, 7, pp. 3334-3340.
European Search Report for Application No. 20860517.0 dated Sep. 18, 2023.
Co-pending Application U.S. Appl. No. 18/853,731, filed Oct. 3, 2024; Janka et al.
USPTO Office Action dated Mar. 18, 2026 received in co-pending U.S. Appl. No. 18/560,953.
Co-pending Application U.S. Appl. No. 18/293,923, filed Jan. 31, 2024.
USPTO Office Action dated Mar. 18, 2026 received in co-pending U.S. Appl. No. 18/293,923.
USPTO Office Action dated Jun. 2, 2026 received in co-pending U.S. Appl. No. 18/560,961.
Notification of Transmittal of The International Search Report and The Written Opinion of the International Searching Authority, or the Declaration; International Application No. PCT/US2022/038502 with a mailing date of Nov. 7, 2022.
Notification of Transmittal of The International Search Report and The Written Opinion of the International Searching Authority, or the Declaration; International Application No. PCT/US2023/065660 with a mailing date of Aug. 7, 2023.
Stanley-Wood, N.; "Particle size analysis: Introduction"; Encyclopedia of Analytical Chemistry; 2000, pp. 1-37.
European Search Report for Application No. 22805201.5 dated Apr. 14, 2025.
European Search Report for Application No. 23789122.1 dated Jun. 19, 2026.

* cited by examiner

MOTHER LIQUOR COMPOSITION GENERATED IN MCFC PROCESS

CROSS-REFERENCE TO RELATED APPLICATION(S)

This application is a national stage filing under 35 USC § 371 of International Application Number PCT/US2022/028900, filed on, May 12, 2022 which claims the benefit of the filing date to U.S. Provisional Application No. 63/201,949, filed on May 20, 2021, the entire disclosures of which are incorporated by reference herein.

TECHNICAL FIELD

The invention generally relates to the field of organic chemistry. It particularly relates to a process for preparing 5-(alkoxycarbonyl)furan-2-carboxylic acids (ACFC) and compositions containing such acids.

BACKGROUND

Aromatic dicarboxylic acids, such as terephthalic acid and isophthalic acid, are used to produce a variety of polyesters. Examples of such polyesters include polyethylene terephthalate (PET) and its copolymers. These aromatic dicarboxylic acids are typically synthesized by catalytically oxidizing the corresponding dialkyl aromatic compounds, which are obtained from fossil fuels.

There is a growing interest in using renewable resources as feedstocks in the chemical industry, mainly due to the progressive reduction of fossil reserves and their related environmental impact. Furan-2,5-dicarboxylic acid (FDCA) and ACFC are versatile intermediates considered to be promising, closest bio-based alternatives to terephthalic acid and isophthalic acid. Like aromatic diacids, ACFC and FDCA can be condensed with diols, such as ethylene glycol, to make polyester resins similar to PET.

Thus, there is a need in the art to provide alternative and/or improved processes for producing carboxylic acid compositions, especially those containing ACFC. There is also a need to provide ACFC compositions having high purity and low color.

The present invention addresses this need as well as others, which will become apparent from the following description and the appended claims.

SUMMARY

In an embodiment of the invention, a process for preparing a compound of the structural formula (I):

(I)

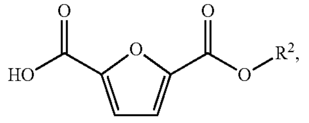

the process comprises contacting a compound of the structural formula (II):

(II)

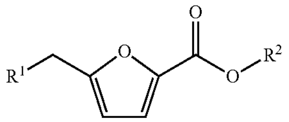

with an oxidizing agent in the presence of an oxidation catalyst and a solvent, wherein:

- the oxidation catalyst comprises cobalt, manganese, and bromine;
- the solvent comprises a monocarboxylic acid having 2 to 6 carbon atoms;
- $R^1$ is hydrogen, $R^3O$—, or $R^3C(O)O$—;
- $R^2$ is an alkyl group having 1 to 6 carbon atoms; and
- $R^3$ is hydrogen or an alkyl group having 1 to 6 carbon atoms;
- wherein $R^3$ is hydrogen or an alkyl group having 1 to 3 carbon atoms, and wherein $R^2$ is not a methyl group; and said mother liquor stream in a solvent recovery zone to form an impurity rich waste stream; and routing a portion of said impurity rich waste stream to a solid-liquid separation zone to form a purge mother liquor stream and optionally wherein a portion of said solvent is recycled from purge process. Also provided is a process to produce compositions thereof.

DETAILED DESCRIPTION

Figure 1:
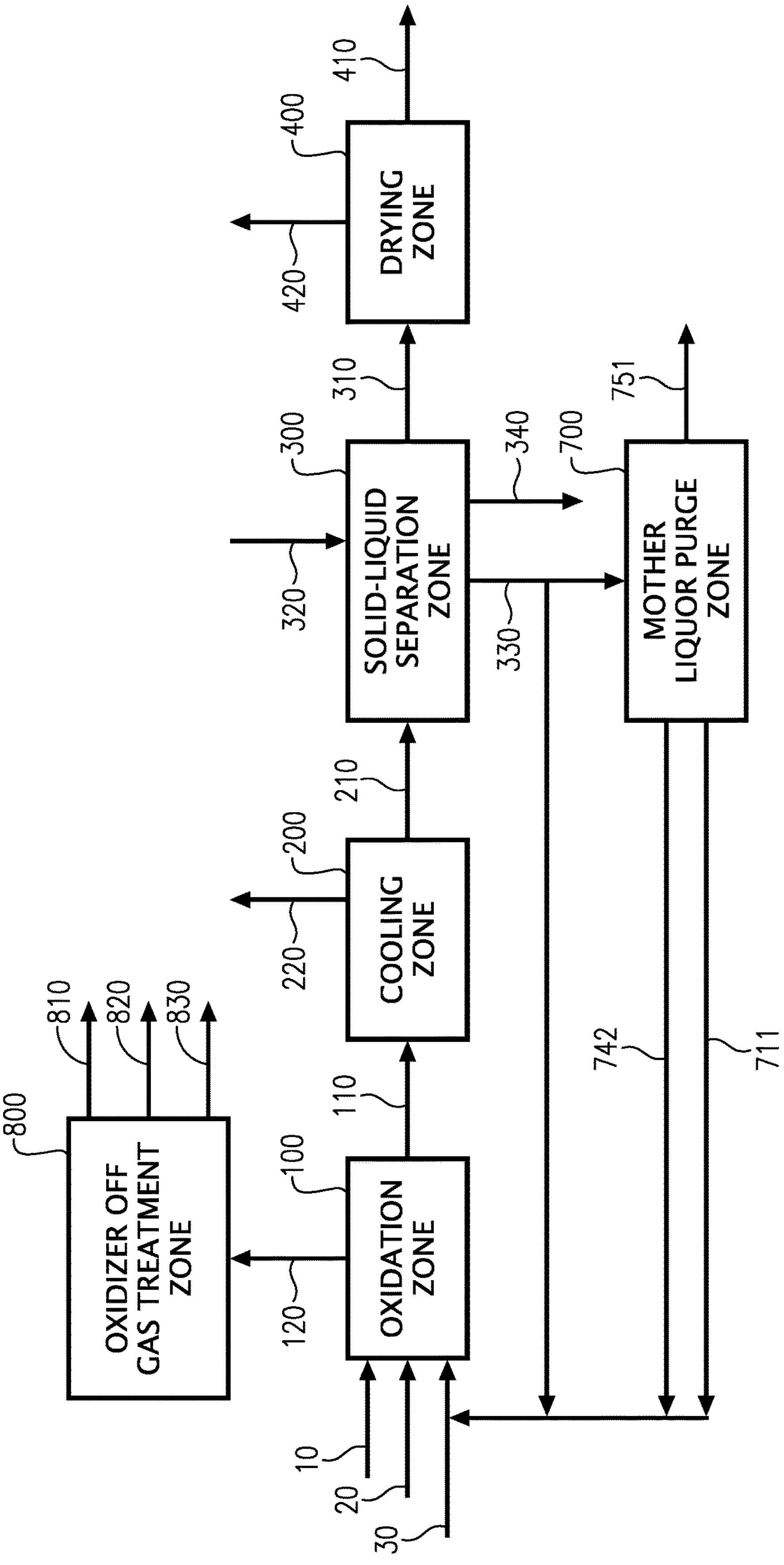
FIG. 1 illustrates different embodiments of the invention wherein a process to produce a dried carboxylic acid 410 is provided.

In one aspect, the invention provides a process for preparing a compound of the structural formula (I):

(I)

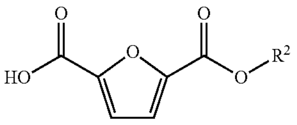

where $R^2$ is an alkyl group having 1 to 6 carbon atoms. The alkyl group may be branched or straight-chained. Examples of such groups include methyl, ethyl, propyl, isopropyl, butyl, methylpropyl, pentyl, ethylpropyl, hexyl, methylpentyl, and ethylbutyl.

In various embodiments, $R^2$ is an alkyl group having 1 to 3 carbon atoms.

In various other embodiments, $R^2$ is methyl.

The compound (I) may be referred to as 5-(alkoxycarbonyl)furan-2-carboxylic acid (ACFC). When $R^2$ is methyl, the compound (I) is 5-(methoxycarbonyl)furan-2-carboxylic acid (MCFC).

The process for preparing compound (I) comprises contacting a compound of the structural formula (II):

(II)

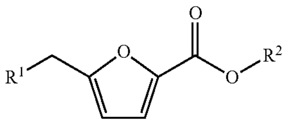

with an oxidizing agent in the presence of an oxidation catalyst and a solvent.

$R^1$ in formula (II) is hydrogen, $R^3O$—, or $R^3C(O)O$— where $R^3$ is hydrogen or an alkyl group having 1 to 6 carbon atoms. As with $R^2$, the alkyl group in $R^3$ may be branched or straight-chained.

In various embodiments, $R^3$ is hydrogen or an alkyl group having 1 to 3 carbon atoms.

In various other embodiments, $R^1$ is hydrogen.

In yet various other embodiments, $R^1$ is $R^3O$— where $R^3$ is hydrogen, methyl, ethyl, propyl, or isopropyl.

In yet various other embodiments, $R^1$ is $R^3C(O)O$— where $R^3$ is hydrogen, methyl, ethyl, propyl, or isopropyl.

$R^2$ in formula (II) is the same as that in formula (I), i.e., an alkyl group having 1 to 6 carbon atoms, or 1 to 3 carbon atoms, or methyl.

Specific examples of the compounds (II) include the following:

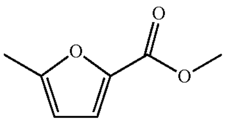

methyl-5-methylfuran-2-carboxylate (MMFC)

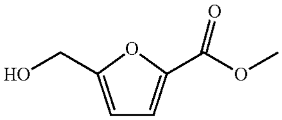

methyl-5-(hydroxymethyl) furan-2-carboxylate

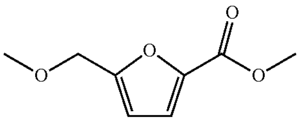

methyl 5-(methoxymethyl) furan-2-carboxylate

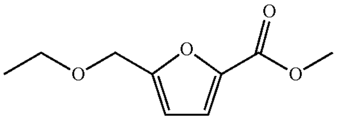

methyl 5-(ethoxymethyl) furan-2-carboxylate

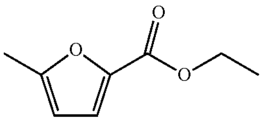

ethyl 5-methylfuran-2-carboxylate

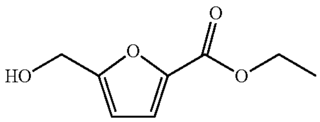

ethyl 5-(hydroxymethyl) furan-2-carboxylate

-continued

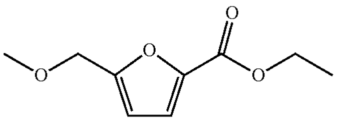

ethyl 5-(methoxymethyl) furan-2-carboxylate

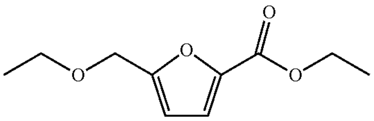

ethyl 5-(ethoxymethyl) furan-2-carboxylate

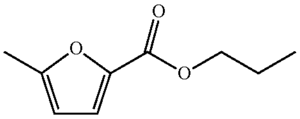

propyl 5-methylfuran-2-carboxylate

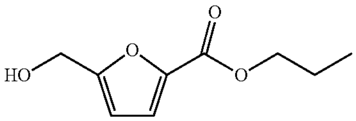

propyl 5-(hydroxymethyl) furan-2-carboxylate

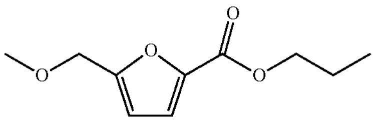

propyl 5-(methoxymethyl) furan-2-carboxylate

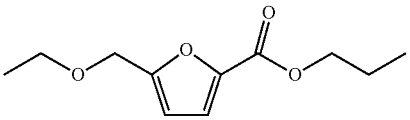

propyl 5-(ethoxymethyl) furan-2-carboxylate

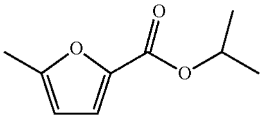

isopropyl 5-methylfuran-2-carboxylate

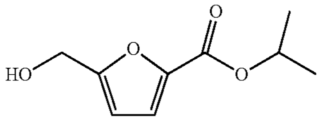

isopropyl 5-(hydroxymethyl) furan-2-carboxylate

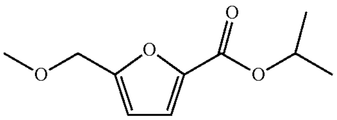

isopropyl 5-(methoxymethyl) furan-2-carboxylate

-continued

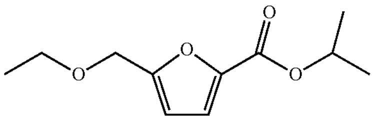

isopropyl 5-(ethoxymethyl)
furan-2-carboxylate

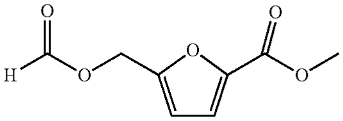

methyl 5-((formyloxy)methyl)
furan-2-carboxylate

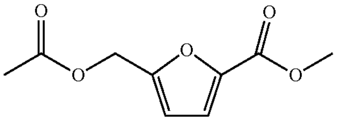

methyl 5-(acetoxymethyl)
furan-2-carboxylate

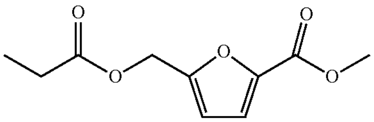

methyl 5-((propionyloxy)methyl)
furan-2-carboxylate

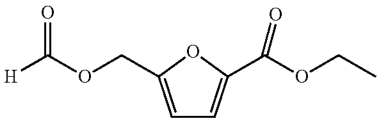

ethyl 5-((formyloxy)methyl)
furan-2-carboxylate

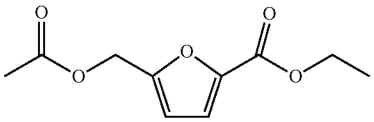

ethyl 5-(acetoxymethyl)
furan-2-carboxylate

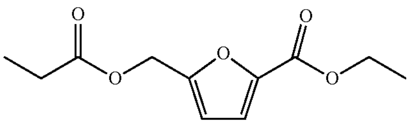

methyl 5-((propionyloxy)methyl)
furan-2-carboxylate

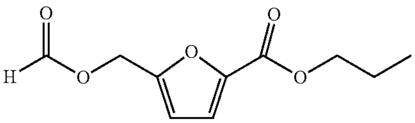

propyl 5-((formyloxy)methyl)
furan-2-carboxylate

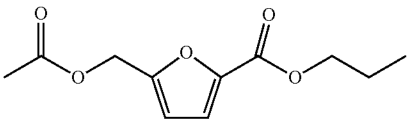

propyl 5-(acetoxymethyl)
furan-2-carboxylate

-continued

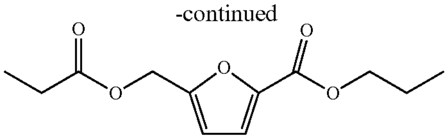

propyl 5-((propionyloxy)methyl)
furan-2-carboxylate

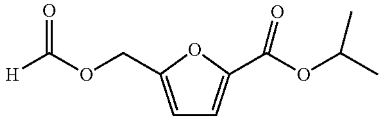

isopropyl 5-((formyloxy)methyl)
furan-2-carboxylate

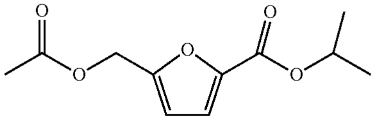

isopropyl 5-(acetoxymethyl)
furan-2-carboxylate

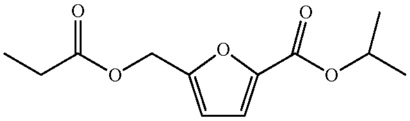

isopropyl 5-((propionyloxy)methyl)
furan-2-carboxylate

In various embodiments, the compound (II) may be selected from methyl 5-methylfuran-2-carboxylate (MMFC), methyl 5-(hydroxymethyl)furan-2-carboxylate, methyl 5-(methoxymethyl)furan-2-carboxylate, methyl 5-(ethoxymethyl)furan-2-carboxylate, ethyl 5-methylfuran-2-carboxylate, ethyl 5-(hydrethylthyl)furan-2-carboxylate, ethyl 5-(methoxymethyl)furan-2-carboxylate, ethyl 5-(ethoxymethyl)furan-2-carboxylate, propyl 5-methyl-furan-2-carboxylate, propyl 5-(hydroxymethyl)furan-2-carboxylate, propyl 5-(methoxymethyl)furan-2-carboxylate, propyl 5-(ethoxymethyl)furan-2-carboxylate, isopropyl 5-methylfuran-2-carboxylate, isopropyl 5-(hydroxymethyl) furan-2-carboxylate, isopropyl 5-(methoxymethyl)furan-2-carboxylate, methyl 5-((formyloxy)methyl)furan-2-carboxylate, methyl 5-(acetoxymethyl)furan-2-cayboxylate, methyl 5-((propionyloxy)methyl)furan-2-carboxylate, ethyl 5-((formyloxy)methyl)furan-2-carboxylate, ethyl 5-(acetoxymethyl)furan-2-cayboxylate, ethyl 5-((propionyloxy) methyl)furan-2-carboxylate, propyl 5-((formyloxy)methyl) furan-2-carboxylate, propyl 5-(acetoxymethyl)furan-2-cayboxylate, propyl 5-((propionyloxy)methyl)furan-2-carboxylate, isopropyl 5-((formyloxy)methyl)furan-2-carboxylate, isopropyl 5-(acetoxymethyl)furan-2-cayboxylate, isopropyl 5-((propionyloxy)methyl)furan-2-carboxylate, isopropyl 5-(ethoxymethyl)furan-2-carboxylate, and mixtures thereof.

In various other embodiments, the compound (II) may be selected from methyl 5-methylfuran-2-carboxylate (MMFC), methyl 5-(hydroxymethyl)furan-2-carboxylate, methyl 5-(methoxymethyl)furan-2-carboxylate, methyl 5-(ethoxymethyl)furan-2-carboxylate, methyl 5-((formyloxy)methyl)furan-2-carboxylate, methyl 5-(acetoxymethyl) furan-2-cayboxylate, methyl 5-((propionyloxy)methyl) furan-2-carboxylate, and mixtures thereof.

In yet various other embodiments, the compound (II) includes methyl 5-methylfuran-2-carboxylate (MMFC).

The compound (II) may be prepared from renewable feedstocks by literature methods and/or may be obtained commercially, such as from xF Technologies Inc.

The oxidizing agent useful in the present process is not particularly limiting. It refers to a source of oxygen. Preferably, the oxidizing agent is an oxygen-containing gas. Examples include molecular oxygen, air, and other oxygen-containing gas. The oxygen-containing gas introduced into the reactor can have from 5 to 80 mole %, from 5 to 60 mole %, from 5 to 45 mole %, or from 15 to 25 mole % of molecular oxygen. The balance of the oxygen-containing gas may be one or more gases inert to oxidation, such as nitrogen and argon.

The oxidation catalyst comprises cobalt, manganese, and bromine. The cobalt, manganese, and bromine may be supplied by any suitable source. The catalyst components are typically sourced from compounds that are soluble in the solvent under reaction conditions or are soluble in the reactant(s) fed to the oxidation zone. Preferably, the sources of the catalyst components are soluble in the solvent at 25 °C, 30 °C, or 40 °C, and 1 atm, and/or are soluble in the solvent under reaction conditions.

The cobalt may be provided in ionic form as inorganic cobalt salts, such as cobalt bromide, cobalt nitrate, or cobalt chloride; or as organic cobalt compounds, such as cobalt salts of aliphatic or aromatic acids having 2-22 carbon atoms, including cobalt acetate, cobalt octanoate, cobalt benzoate, cobalt acetylacetonate, and cobalt naphthalate.

The oxidation state of cobalt when added as a compound to the reaction mixture is not limited and includes both the +2 and +3 oxidation states.

The manganese may be provided as one or more inorganic manganese salts, such as manganese borates, manganese halides, manganese nitrates; or as organometallic manganese compounds, such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrogen bromide, hydrobromic acid (sometimes referred to as aqueous hydrogen bromide or aqueous HBr), sodium bromide, potassium bromide, ammonium bromide, and tetrabromoethane. Hydrobromic acid or sodium bromide may be preferred bromine sources.

The cobalt can used in amounts ranging from 2 to 10,000 ppmw, from 500 to 6,000 ppmw, from 1,000 to 6,000 ppmw, from 700 to 4,500 ppmw, or from 1,000 to 4,000 ppmw.

The manganese can be used in amounts ranging from 2 to 10,000 ppmw, from 2 to 600 ppmw, from 20 to 400 ppmw, or from 20 to 200 ppmw.

The bromine can be used in amounts ranging from 2 to 10,000 ppmw, from 300 to 4,500 ppmw, from 700 to 4,000 ppmw, or from 1,000 to 4,000 ppmw.

These exemplary ranges of Co, Mn, and Br are based on the total weight of the reaction mixture.

Alternatively, the catalyst amounts may be expressed based on the weight of the raw material, i.e., the compound (II). In which case, the reaction may be performed with, for example, a cobalt content of 0.50 to 5.0 wt %, an Mn content of 0.15 to 3.0 wt %, and a Br content of 0.11 to 3.2 wt %, based on the weight of compound (II).

In various embodiments, the cobalt content can range from 0.50 to 1.0 wt %, the Mn content can range from 1.5 to 2.3 wt %, and the bromine content can range from 0.32 to 3.2 wt %, based on the weight of compound (II).

In various embodiments, the weight ratio of cobalt to manganese in the oxidation catalyst can be at least 0.01:1, at least 0.1:1, at least 1:1, at least 10:1, at least 20:1, at least 50:1, at least 100:1, or at least 400:1.

In various other embodiments, the weight ratio of Co:Mn in the oxidation catalyst can range from 1:1 to 400:1, from 10:1 to 400:1, or from 20:1 to 400:1.

In yet various other embodiments, the weight ratio of Co:Mn in the oxidation catalyst can range from 0.1:1 to 100:1, from 0.1:1 to 10:1, from 0.1:1 to 1:1, from 1:1 to 100:1, from 10:1 to 100:1, or from 20:1 to 100:1.

In various embodiments, the weight ratio of cobalt to bromine can vary from 0.7:1 to 3.5:1, from 0.5:1 to 10:1, or from 0.5:1 to 5:1.

The above ratios of Co:Mn and Co:Br can generate a high yield of ACFC, decrease the formation of impurities, including those causing color in the product (as measured by b*), and/or keep the amount of CO and $CO_2$ in the off-gas to a minimum.

The solvent for the reaction comprises a monocarboxylic acid having 2 to 6 carbon atoms or from 2 to 4 carbon atoms. Examples of such acids include acetic acid, propionic acid, n-butyric acid, isobutyric acid, n-valeric acid, trimethylacetic acid, and caprioic acid. Mixtures of such acids may be used as well as mixtures of one or more of the acids with water. The solvent may be selected based on its ability to solubilize the catalyst components under the reaction conditions. The solvent may also be selected based on its volatility under the reaction conditions so as to allow it to be taken as an off-gas from the oxidation reactor.

In various embodiments, the solvent comprises anhydrous acetic acid, mixtures of peracetic acid and acetic acid, mixtures of acetic acid and water, or mixtures of peracetic acid, acetic acid, and water.

In various other embodiments, the solvent used for the oxidation is an aqueous acetic acid solution, typically having a concentration of 50 to 99 wt %, 75 to 99 wt %, or 80 to 99 wt % of acetic acid.

The solvent and catalyst used in the process may be recycled and reused. For example, a crude ACFC composition may be discharged from the oxidation reactor and subjected to a variety of mother liquor exchange, separation, purification, and/or recovery methods. These methods can provide recovered solvent and catalyst components for recycling back to the oxidation reactor. Thus, a portion of the solvent introduced into the oxidation reactor may be from a recycle stream obtained by displacing, for example, from 80 to 90 wt % of the mother liquor in the crude reaction mixture discharged from the oxidation reactor. The mother liquor may be displaced with fresh, wet acetic acid, for example, acetic acid containing from greater than 0 to 20 wt %, or from greater than 0 to 15 wt %, of water.

Generally, the oxidation reaction can be carried out at a temperature from 50 °C to 220 °C, from 75 °C to 200 °C, from 75 °C to 180 °C, from 100 °C to 180 °C, from 110 °C to 180 °C, from 130 °C to 180 °C, from 100 °C to 160 °C, from 110 °C to 160 °C, or from 130 °C to 160 °C. The typical oxidization reactor can be characterized by a lower section where gas bubbles are dispersed in a continuous liquid phase. Solids can also be present in the lower section. In the upper section of the reactor, gas is the continuous phase where entrained liquid drops can also be present. These oxidation temperatures refer to the temperature of the reaction mixture inside the oxidation reactor where liquid is present as the continuous phase.

In various embodiments, the liquid phase in the oxidation reactor has a pH from −4.0 to 2.0.

Generally, the oxidation reaction can be carried out with a pressure above the reaction mixture of, for example, 50 to 1,000 psig, 50 to 750 psig, 50 to 500 psig, 50 to 400 psig, 50 to 200 psig, 100 to 1000 psig, 100 to 750 psig, 100 to 500 psig, 100 to 400 psig, 100 to 300 psig, or 100 to 200 psig. The pressure is typically selected such that the solvent is mainly in the liquid phase.

The oxidation process may be carried out in a batch, semi-continuous (sometimes referred to as semi-batch), or continuous mode. A batch process typically involves adding the entire amount of the compound (II) feedstock, the catalyst, and the solvent into the reactor before starting the reaction, passing an oxidizing gas through the reaction mixture to initiate and perform the reaction, and recovering the reaction mixture all at once at the end of the reaction.

A semi-continuous process typically involves adding the entire amount of the catalyst and the solvent into the reactor, continuously introducing the compound (II) feedstock and the oxidizing gas to the reactor to carry out the oxidation reaction, and recovering the reaction mixture all at once at the end of the reaction.

A continuous process typically involves continuously introducing the raw material, the catalyst, the solvent, and the oxidizing gas into the reactor to carry out the oxidation reaction and continuously recovering the reaction mixture containing the product compound (I).

The oxidation reaction time can vary, depending on various factors such as the temperature, pressure, and catalyst composition/concentration employed. But typically, the reaction time can range from 1 to 6 hours or from 1 to 3 hours.

The present process can produce compound (1) in a yield of at least 50%, at least 60%, at least 70%, at least 80%, at least 85%, at least 90%, at least 95%, at least 98%, at least 99%, or at least 99.5%.

Yield can be calculated by dividing the mass of the ACFC (compound (1)) obtained by the theoretical amount of the oxidable raw material (compound (II)) that should be produced based on the amount of raw material that has been consumed. For example, in the case of MMFC as the compound (II), if one mole or 140.1 grams of MMFC are oxidized, it would theoretically generate one mole or 170.1 grams of MCFC. If, for example, the actual amount of MCFC formed is only 150 grams, the yield of MCFC for this reaction would be 88.2% (=150/170.1×100). The same calculation can be made for an oxidation reaction using other oxidizable compounds as well as to other products/byproducts.

In addition to the compound (1), the present process can produce one or more byproducts. These byproducts can include furan-2,5-dicarboxylic acid (FDCA), 5-formylfuran-2-carboxylic acid (FFCA), and alkyl 5-formylfuran-2-carboxylate (AFFC). When $R^2$ in the starting compound (II) is methyl, the AFFC is methyl 5-formylfuran-2-carboxylate (MFFC). The structural formulas of FDCA, FFCA, AFFC, and MFFC are provided below.

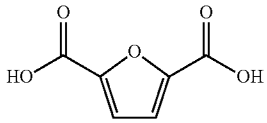

(FDCA)

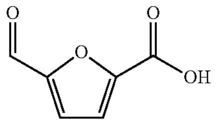

(FFCA)

-continued

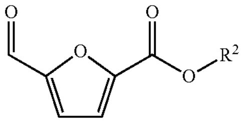

(AFFC)

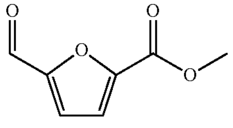

(MFFC)

In various embodiments, the present process produces FDCA in yields of less than 20%, less than 15%, less than 10%, less than 5%, less than 1%, or less than 0.5%.

In the present process, the extent of solvent burned and rendered unusable, as estimated by carbon oxides formation, can be the same as, or even lower than, typical oxidation processes. Even though the absolute amount of carbon oxides formation may be reduced by known techniques, this reduction can be achieved without risking an acceptable conversion. Obtaining a low amount of carbon oxides formation may generally be achieved by running the reaction at lower oxidation temperatures and/or using a catalyst that has a lower degree of conversion or selectivity, but this typically results in decreased conversion and increased quantities of intermediates. The present process, however, can have the advantage of maintaining a low ratio of solvent burn to conversion, thereby minimizing the impact on conversion to obtain the low solvent burn relative to other oxidation processes.

Thus, in various embodiments, the ratio of carbon oxides formation (in moles of CO and $CO_2$ expressed as $CO_x$, per mole of compound (II) feed), can be no more than 1.0 mole $CO_x$, or no more than 0.5 mole $CO_x$, or no more than 0.3 mole $CO_x$, in each case with respect to the molar quantity of the compound (II) fed into the reactor.

At the end of the reaction, the reaction mixture is typically depressurized and cooled to obtain a slurry comprising the product compound (1). The product slurry may undergo one or more solid-liquid separation (such as filtration and/or centrifugation) and washing steps to obtain a wet cake. The wet cake may then be dried (optionally at elevated temperature and under vacuum) to obtain a dried, solid product composition.

In various embodiments, the present process may include one or more steps to obtain a dried, solid product composition comprising the compound (I).

These steps include at the conclusion of the oxidation reaction, passing at least a portion of the oxidation reaction mixture to a crystallization zone to form a crystallized slurry. Generally, the crystallization zone comprises at least one crystallizer. In the crystallization zone, the reaction mixture may be cooled to a temperature from 20 °C to 175 °C, 40 °C to 175 °C, 50 °C to 170 °C, 60 °C to 165 °C, 25 °C to 100 °C, or from 25 °C to 50 °C, to form the crystallized slurry. Vapor from the crystallization zone can be condensed in at least one condenser and returned to the crystallization zone or routed away from crystallization zone. Alternatively, vapor from the crystallization zone can be recycled without condensation or sent to an energy recovery device. As another option, the crystallizer vapor can be withdrawn and routed to a recovery system where the solvent is removed and recycled, and any VOCs may be treated, for example, by incineration in a catalytic oxidation unit.

The crystallized slurry may be further cooled in a cooling zone to generate a cooled, crystallized slurry. The cooling can be accomplished by any means known in the art. Typically, the cooling zone comprises a flash tank. The temperature of the cooled, crystallized slurry can range from 20 °C to 160 °C, from 35 °C to 160 °C, from 20 °C to 140 °C, from 50 °C to 140 °C, from 20 °C to 120 °C, from 25 °C to 120 °C, from 45 °C to 120 °C, from 70 °C to 120 °C, from 55 °C to 95 °C, from 75 °C to 95 °C, or from 20 °C to 70 °C .

In various embodiments, at least a portion (up to 100%) of the oxidation mixture can be routed directly to the cooling zone without first passing through the crystallization zone.

In various other embodiments, at least a portion (up to 100%) of the crystallized slurry can be routed directly to a solid-liquid separation zone without first passing through the cooling zone.

The cooled, crystallized slurry may be passed to a solid-liquid separation zone. The solid-liquid separation zone typically comprises one or more solid-liquid separation devices configured to separate solids from liquids. In the solid-liquid separation zone, the solids may be washed with a wash solvent and dewatered by reducing the moisture content in the washed solids to less than 30 wt %, less than 25 wt %, less than 20 wt %, less than 15 wt %, or less than 10 wt %.

Equipment suitable for the solid-liquid separation zone typically include centrifuges, cyclones, rotary drum filters, belt filters, pressure leaf filters, candle filters, etc.

In various embodiments, the solid-liquid separation zone includes a rotary pressure drum filter.

The wash solvent comprises a liquid suitable for displacing and washing mother liquor from the solids.

In various embodiments, the wash solvent comprises acetic acid and water.

In various other embodiments, the wash solvent comprises water (up to 100%).

The temperature of the wash solvent can range from 20 °C to 135 °C, from 40 °C to 110 °C, from 50 °C to 90 °C, or from 20 °C to 70 °C. The amount of wash solvent used can be characterized as the wash ratio, which corresponds to the mass of the wash liquid divided by the mass of the solids on a batch or continuous basis. The wash ratio can range from 0.3 to 5, from 0.4 to 4, or from 0.5 to 3.

After the solids are washed in the solid-liquid separation zone, they are typically dewatered to generate a purified, wet cake. Dewatering involves reducing the moisture content of the solids to less than 30 wt %, less than 25 wt %, less than 20 wt %, less than 15 wt %, or less than 10 wt %.

In various embodiments, dewatering is accomplished in a filter by passing a gas stream through the solids to displace free liquid after the solids have been washed with a wash solvent.

In various other embodiments, dewatering is achieved by centrifugal forces in a perforated- or solid-bowl centrifuge.

The filtrate generated in the solid-liquid separation zone is a mother liquor comprising the oxidation solvent, the catalyst, and some impurities/oxidation byproducts. The filtrate can be routed to a purge zone or back to the oxidation reactor or both.

In the purge zone, a portion of the impurities present in the mother liquor can be isolated and removed. The remaining solvent and catalyst can be isolated and recycled to the oxidation reactor.

In various embodiments, the remaining solvent from the purge zone can contain greater than 30%, greater than 50%, greater than 70%, or greater than 90% of the catalyst that entered the purge zone on a continuous or batch basis.

Wash liquor from the solid-liquid separation zone typically comprises a portion of the mother liquor and wash solvent. The ratio of mother liquor mass to wash solvent mass can be less than 3 or less than 2.

The purified, wet cake from the solid-liquid separation zone may be passed to a drying zone to generate a dry, solid product and a vapor stream. The vapor stream can comprise wash solvent vapor and/or oxidation solvent vapor.

The drying zone typically comprises one or more dryers capable of evaporating at least 10% of the volatiles remaining in the purified, wet cake. Examples of such dryers include indirect contact dryers, such as rotary steam tube dryers, Single-Shaft Porcupine™ dryers, and Bepex Solidaire™ dryers as well as direct contact dryers, such as fluidized-bed dryers and ovens equipped with conveyers.

In various embodiments, a vacuum system can be used to draw the vapor stream from the drying zone. If a vacuum system is used in this fashion, the pressure of the vapor stream at the dryer outlet can range from 760 mm Hg to 400 mm Hg, from 760 mm Hg to 600 mm Hg, from 760 mm Hg to 700 mm Hg, from 760 mm Hg to 720 mm Hg, or from 760 mm Hg to 740 mm Hg, where the pressure is measured in mm Hg above absolute vacuum.

The process according to the invention can produce a dried, solid product containing the compound (I) that is surprisingly pure and low in color, without the need to perform reactive purification steps, such as secondary oxidations (sometimes referred to as post-oxidation), hydrogenations, and/or treatments with an oxidizer (such as sodium hypochlorite and/or hydrogen peroxide).

In a batch process, secondary oxidation refers to the step of continuing to supply the oxidizing gas to the reactor after the absorption of oxygen in the reaction medium has stopped. In a semi-continuous or continuous process, secondary oxidation refers to the step of continuing to supply of the oxidizing gas to the reaction zone when the supply of the compound (II) feedstock is stopped.

Thus, in a second aspect, the invention provides a dried, solid composition comprising at least 70 wt % of a compound of the structural formula (I):

(I)

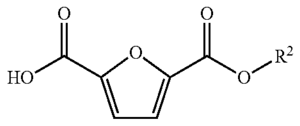

wherein $R^2$ is defined herein above and the wt % of compound (I) is based on the total weight of the composition.

In various embodiments, the dried, solid composition comprises at least 80 wt %, at least 90 wt %, at least 95 wt %, at least 97 wt %, at least 98 wt %, at least 99 wt %, or at least 99.5 wt % of the compound (1), based on the total weight of the composition.

In various embodiments, the dried, solid composition comprises less than 30 wt %, less than 20 wt %, less than 10 wt %, less than 5 wt %, less than 3 wt %, less than 2 wt %, less than 1 wt %, or less than 0.05 wt % of furan-2,5-dicarboxylic acid (FDCA), based on the total weight of the composition. In each case, the content of FDCA may be greater than 0 wt %.

In various embodiments, the dried, solid composition comprises less than 1 wt %, less than 0.5 wt %, less than 0.3 wt %, less than 0.1 wt %, less than 500 ppmw, less than 400 ppmw, less than 300 ppmw, less than 200 ppmw, less than 100 ppmw, less than 50 ppmw, less than 10 ppmw, less than 5 ppmw, or less than 1 ppmw of 5-formylfuran-2-carboxylic acid (FFCA), based on the total weight of the composition. In each case, the content of FFCA may be greater than 0 wt %.

In various embodiments, the dried, solid composition comprises less than 1 wt %, less than 0.5 wt %, less than 0.3 wt %, less than 0.1 wt %, less than 500 ppmw, less than 400 ppmw, less than 300 ppmw, less than 200 ppmw, less than 100 ppmw, less than 50 ppmw, or less than 10 ppmw of alkyl 5-formylfuran-2-carboxylate (AFFC), based on the total weight of the composition. In each case, the content of AFFC may be greater than 0 wt %.

When $R^2$ is methyl in compound (1), the dried, solid composition comprises less than 1 wt %, less than 0.5 wt %, less than 0.3 wt %, less than 0.1 wt %, less than 500 ppmw, less than 400 ppmw, less than 300 ppmw, less than 200 ppmw, less than 100 ppmw, less than 50 ppmw, or less than 10 ppmw of methyl 5-formylfuran-2-carboxylate (MFFC), based on the total weight of the composition. In each case, the content of MFFC may be greater than 0 wt %.

In various embodiments, the dried, solid composition can have a b* value of less than 4, less than 2, less than 1, from −1 to +1, or from −0.5 to +0.5.

The b* value is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In one embodiment, the dried, solid composition comprises:

(a) at least 70 wt % of a compound (I);
(b) less than 30 wt % of furan-2,5-dicarboxylic acid (FDCA);
(c) less than 500 ppmw of 5-formylfuran-2-carboxylic acid (FFCA); and
(d) less than 1000 ppmw of alkyl 5-formylfuran-2-carboxylate (AFFC), all amounts are based on the total weight of the composition, and wherein the composition has a b* value of less than 4.

In another embodiment, the dried, solid composition comprises:

(a) at least 70 wt % of 5-(methoxycarbonyl) furan-2-carboxylic acid (MCFC);
(b) less than 30 wt % of furan-2,5-dicarboxylic acid (FDCA);
(c) less than 500 ppmw of 5-formylfuran-2-carboxylic acid (FFCA); and
(d) less than 500 ppmw of methyl 5-formylfuran-2-carboxylate (MFFC), all amounts are based on the total weight of the composition, and wherein the composition has a b* value of less than 4.

In yet another embodiment, the dried, solid composition comprises:

(a) at least 99 wt % of 5-(methoxycarbonyl) furan-2-carboxylic acid (MCFC);
(b) less than 500 ppmw of furan-2,5-dicarboxylic acid (FDCA);
(c) less than 10 ppmw of 5-formylfuran-2-carboxylic acid (FFCA); and
(d) less than 100 ppmw of methyl 5-formylfuran-2-carboxylate (MFFC), all amounts are based on the total weight of the composition, and wherein the composition has a b* value of −1 to +1.

In yet another embodiment, the dried, solid composition comprises:

(a) at least 99 wt % of 5-(methoxycarbonyl) furan-2-carboxylic acid (MCFC);
(b) less than 500 ppmw of furan-2,5-dicarboxylic acid (FDCA);
(c) less than 10 ppmw of 5-formylfuran-2-carboxylic acid (FFCA); and
(d) less than 100 ppmw of methyl 5-formylfuran-2-carboxylate (MFFC), all amounts are based on the total weight of the composition, and wherein the composition has a b* value of −0.5 to +0.5.

In various embodiments, the dried, solid composition is obtained without performing or undergoing a reactive purification step.

In various other embodiments, the dried, solid composition is obtained without performing or undergoing a secondary oxidation step, a hydrogenation step, and/or a treatment step with an oxidizer.

In yet various other embodiments, the dried, solid composition is polymer grade, i.e., it has sufficient purity to be used for making a polymer without performing or undergoing a reactive purification step, such as a secondary oxidation step, a hydrogenation step, and/or a treatment step with an oxidizer.

To remove any doubt, the present invention includes and expressly contemplates and discloses any and all combinations of embodiments, features, characteristics, parameters, and/or ranges mentioned herein. That is, the subject matter of the present invention may be defined by any combination of embodiments, features, characteristics, parameters, and/or ranges mentioned herein.

It is contemplated that any ingredient, component, or step that is not specifically named or identified as part of the present invention may be explicitly excluded.

Any process/method, apparatus, compound, composition, embodiment, or component of the present invention may be modified by the transitional terms "comprising," "consisting essentially of," or "consisting of," or variations of those terms.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered as approximations, unless the context indicates otherwise. These values and ranges may vary from their stated numbers depending upon the desired properties sought to be obtained by the present disclosure as well as the variations resulting from the standard deviation found in the measuring techniques. Moreover, the ranges described herein are intended and specifically contemplated to include all sub-ranges and values within the stated ranges. For example, a range of 50 to 100 is intended to include all values within the range including sub-ranges such as 60 to 90, 70 to 80, etc.

Any two numbers of the same property or parameter reported in the working examples may define a range. Those numbers may be rounded off to the nearest thousandth, hundredth, tenth, whole number, ten, hundred, or thousand to define the range.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following working examples, although it should be understood that these examples are included merely for purposes of illustration and are not intended to limit the scope of the invention.

Additional Disclosure

It should be understood that the following is not intended to be an exclusive list of defined terms. Other definitions may be provided in the foregoing description, such as, for example, when accompanying the use of a defined term in context. This process can also be used for MCFC and ACFC as described above when the appropriate starting material are used. The appropriate starting is described previously as well.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

Figure 2:
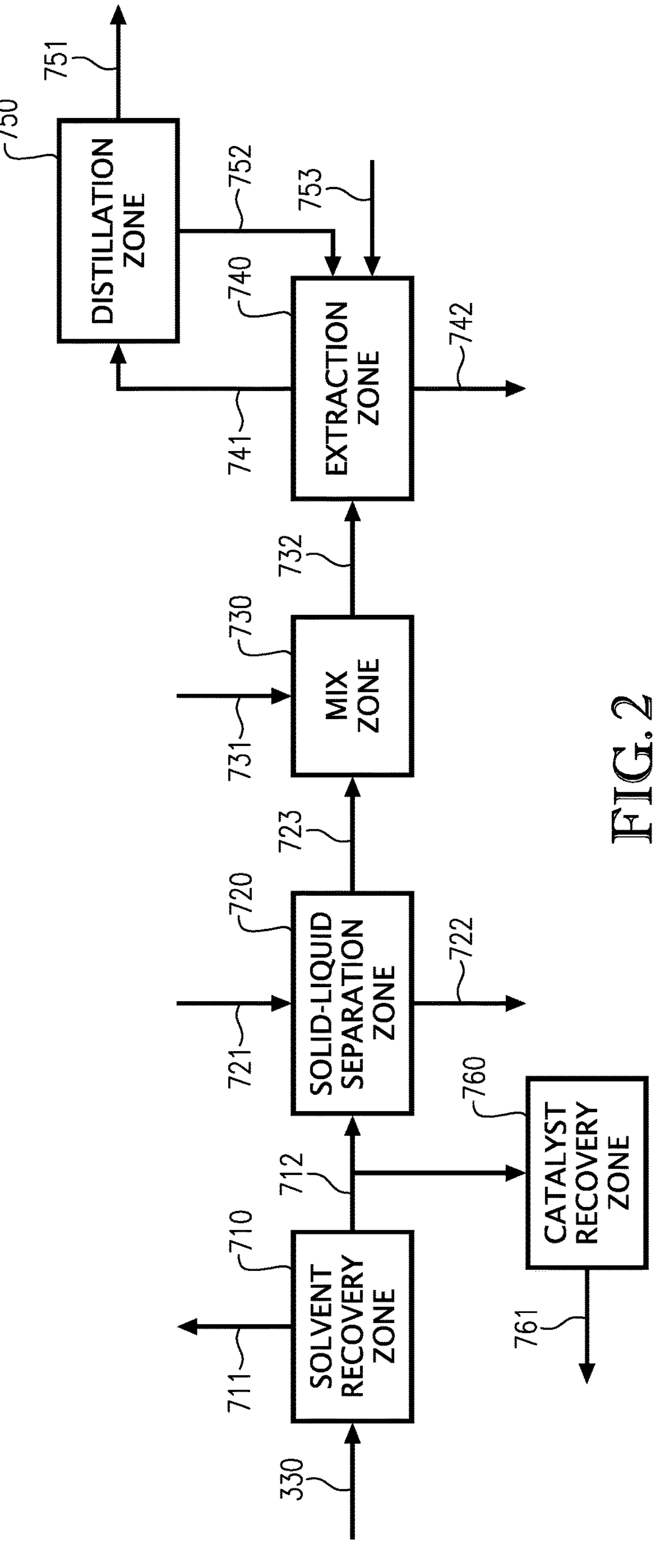
FIG. 2 illustrates an embodiment of the invention, wherein an purge stream is created. This figure is a detailed illustration on zone 700 in FIG. 1.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62 °F, such a description provides literal support for a broad numerical range of 25 °F to 99° F. (62 °F+/−37 °F), an intermediate numerical range of 43 °F to 81 °F (62 °F+/−19 °F), and a narrow numerical range of 53 °F to 71 °F (62 °F+/−9 °F). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively One embodiment of the present invention is illustrated in FIGS. 1 and 2. The present invention provides a process for recovering a portion of oxidation solvent, a portion of oxidation catalyst, and removing a portion of oxidation by-products and raw material impurities from a solvent stream generated in a process to make furan-2,5-dicarboxylic acid (FDCA). The process discussed below can be combined with the previous process in any logical order.

Step (a) comprises feeding oxidation solvent, a catalyst system, a gas stream comprising oxygen, and oxidizable raw material comprising at least one compound selected from the group of formula: 5-(hydroxymethyl)furfural (5-HMF), 5-(chloromethyl)furfural (5-CMF), 2,5-dimethylfuran (2,5-DMF), 5-HMF esters (5-R(CO)O$CH_2$-furfural where R=alkyl, cycloalkyl and aryl), 5-HMF ethers (5-R'O$CH_2$-furfural, where R'=alkyl, cycloalkyl and aryl), 5-alkyl furfurals (5-R"-furfural, where R"=alkyl, cycloalkyl and aryl), alkylcarboxylate of methyfuran (5-R'''O(CO)-methylfuran, where R'''=alkyl, cycloalkyl), alkylcarboxylate of alkoxyfuran (5-R''''O(CO)—OR'''''furan, where R''''=alkyl, cycloalkyl and aryl and R'''''=alkyl, cycloalkyl and aryl), mixed feed-stocks of 5-HMF and 5-HMF esters and mixed feed-stocks of 5-HMF and 5-HMF ethers, mixed feed-stocks of 5-HMF and 5-alkyl furfurals, mixed feed-stocks of 5-HMF and 5-CMF, mixed feed-stocks of 5-HMF and 2,5-DMF, mixed feed-stocks of 5-HMF and alkylcarboxylate of methyfuran, mixed feed-stocks of 5-HMF and alkylcarboxylate of alkoxyfuran to an oxidation zone 100 to generate a crude carboxylic acid slurry 110 comprising furan-2,5-dicarboxylic (FDCA).

Structures for the preferred oxidizable raw material compounds are outlined below:

Preferred 5-HMF Derivative Feeds

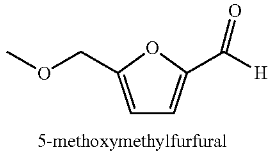

5-methoxymethylfurfural

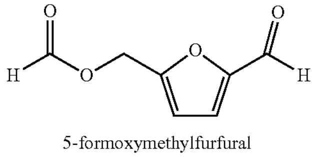

5-formoxymethylfurfural

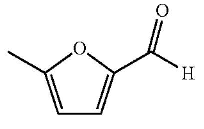

5-methylfurfural

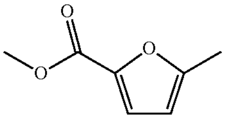

methyl-5-methylfurfural-2-carboxylate

-continued

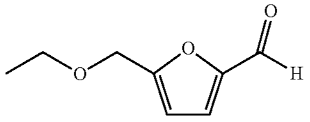

5-ethoxymethylfurfural

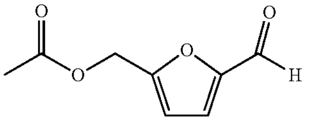

5-acetoxymethylfurfural

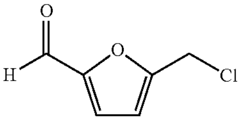

5-(chloromethyl)furfural

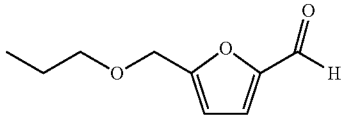

5-propoxymethylfurfural

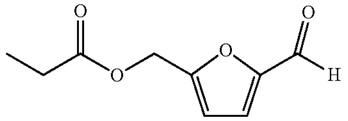

5-propoxymethylfurfural

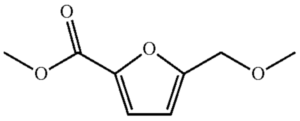

methyl 5-(methoxymethyl)furfural-2-carboxylate

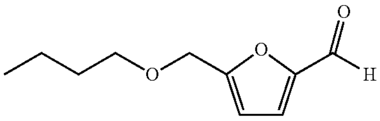

5-butoxymethylfurfural

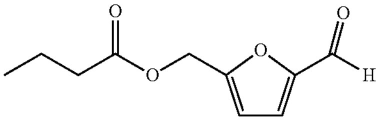

5-butyroxymethylfurfural

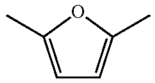

2,5-dimethylfuran

5-HMF feed is oxidized with elemental $O_2$ in a multi-step reaction to form FDCA with 5-formyl furan-2-carboxyic acid (FFCA) as a key intermediate (Eq 1). Oxidation of 5-(acetoxymethyl)furfural (5-AMF), which contains an oxidizable ester and aldehydes moieties, produces FDCA, FFCA, and acetic acid (Eq 2). Similarly, oxidation of 5-(ethoxymethyl)furfural (5-EMF) produces FDCA, FFCA, 5-(ethoxycarbonyl)furan-2-carboxylic acid (EFCA) and acetic acid (Eq 3).

(1)

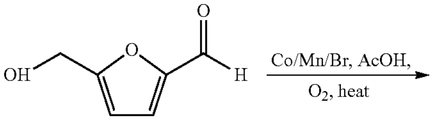

5-HMF

-continued

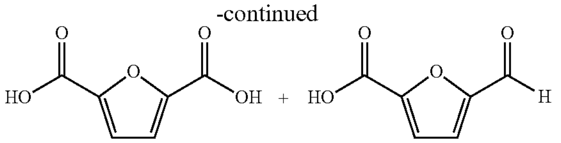

FDCA FFCA (2)

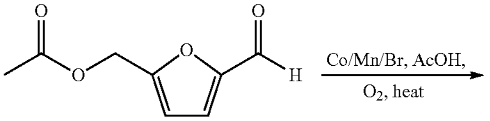

5-AMF

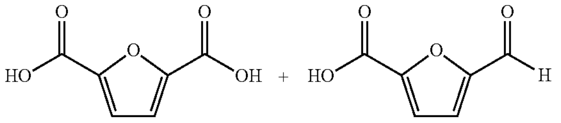

FDCA FFCA (3)

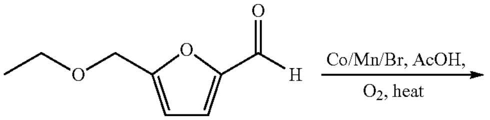

5-EMF

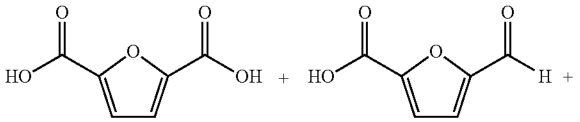

FDCA FFCA

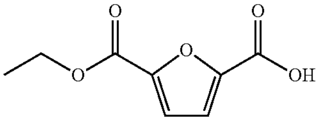

EFCA

Streams routed to the primary oxidation zone 100 comprise gas stream 10 comprising oxygen, and stream 30 comprising oxidation solvent, and stream 20 comprising oxidizable raw material. In another embodiment, streams routed to the oxidization zone 100 comprise gas stream 10 comprising oxygen and stream 20 comprising oxidation solvent, catalyst, and oxidizable raw material. In yet another embodiment, the oxidation solvent, gas comprising oxygen, catalyst system, and oxidizable raw materials can be fed to the oxidization zone 100 as separate and individual streams or combined in any combination prior to entering the oxidization zone 100 wherein said feed streams may enter at a single location or in multiple locations into oxidizer zone 100.

Suitable catalyst systems is at least one compound selected from, but are not limited to, cobalt, bromine, and manganese compounds, which are soluble in the selected oxidation solvent. The preferred catalyst system comprises cobalt, manganese and bromine wherein the weight ratio of cobalt to manganese in the reaction mixture is from about 10 to about 400 and the weight ratio of cobalt to bromine is from about 0.7 to about 3.5. Data shown in Table 1 demonstrate that very high yield of FDCA can be obtained using 5-HMF or its derivatives using the catalyst composition described above.

Suitable oxidation solvents include, but are not limited to, aliphatic mono-carboxylic acids, preferably containing 2 to 6 carbon atoms, and mixtures thereof, and mixtures of these compounds with water. In one embodiment, the oxidation solvent comprises acetic acid wherein the weight % of acetic acid in the oxidation solvent is greater than 50%, greater than 75%, greater than 85%, and greater than 90%. In another embodiment, the oxidation solvent comprises acetic acid and water wherein the proportions of acetic acid to water is greater than 1:1, greater than 6:1, greater than 7:1, greater than 8:1, and greater than 9:1.

The temperature in oxidation zone can range from 100 °C to 220 °C, or 100 °C to 200 °C, or 130 °C to 180 °C, or 100 °C to 180 °C and can preferably range from 110 °C to 160 °C. In another embodiment, the temperature in oxidation zone can range from 105 °C to 140 °C.

One advantage of the disclosed oxidation conditions is low carbon burn as illustrated in Table 1. Oxidizer off gas stream 120 is routed to the oxidizer off gas treatment zone 800 to generate an inert gas stream 810, liquid stream 820 comprising water, and a recovered oxidation solvent stream 830 comprising condensed solvent. In one embodiment, at least a portion of recovered oxidation solvent stream 830 is routed to wash solvent stream 320 to become a portion of the wash solvent stream 320 for the purpose of washing the solids present in the solid-liquid separation zone. In another embodiment, the inert gas stream 810 can be vented to the atmosphere. In yet another embodiment, at least a portion of the inert gas stream 810 can be used as an inert gas in the process for inerting vessels and or used for convey gas for solids in the process. In another embodiment, at least a portion of the energy in stream 120 is recovered in the form of steam and or electricity.

In another embodiment of the invention, a process is provided for producing furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, oxidation solvent stream 20, and at least one catalyst system in a oxidation zone 100; wherein the oxidizable compound is 5-(hydroxymethyl)furfural (5-HMF); wherein the solvent stream comprises acetic acid with or without the presence of water; wherein the catalyst system comprising cobalt, manganese, and bromine, wherein the weight ratio of cobalt to manganese in the reaction mixture is from about 10 to about 400. In this process, the temperature can vary from about 100 °C to about 220 °C, from about 105 °C to about 180 °C, and from about 110 °C to about 160 °C. The cobalt concentration of the catalyst system can range from about 1000 ppm to about 6000 ppm, and the amount of manganese can range from about 2 ppm to about 600 ppm, and the amount of bromine can range from about 300 ppm to about 4500 ppm with respect to the total weight of the liquid in the reaction medium.

Step (b) comprises routing the crude carboxylic acid slurry 110 comprising FDCA to cooling zone 200 to generate a cooled crude carboxylic acid slurry stream 210 and a $1^{st}$ vapor stream 220 comprising oxidation solvent vapor. The cooling of crude carboxylic slurry stream 110 can be accomplished by any means known in the art. Typically, the cooling zone 200 comprises a flash tank. In another embodiment, a portion up to 100% of the crude carboxylic acid slurry stream 110 is routed directly to solid-liquid separation zone 300, thus said portion up to 100% is not subjected to cooling in cooling zone 200. The temperature of stream 210 can range from 35 °C to 210 °C, 55 °C to 120 °C, and preferably from 75 °C to 95 °C.

Step (c) comprises isolating, washing, and dewatering solids present in the cooled crude carboxylic acid slurry stream 210 in the solid-liquid separation zone 300 to generate a crude carboxylic acid wet cake stream 310 comprising FDCA. These functions may be accomplished in a single solid-liquid separation device or multiple solid-liquid separation devices. The solid-liquid separation zone comprises at least one solid-liquid separation device capable of separating solids and liquids, washing solids with a wash solvent stream 320, and reducing the % moisture in the washed solids to less than 30 weight %, less than 20 weight %, less than 15 weight %, and preferably less than 10 weight %.

Equipment suitable for the solid liquid separation zone can typically be at least one of the following types of devices: centrifuge, cyclone, rotary drum filter, belt filter, pressure leaf filter, candle filter, and the like. The preferred solid liquid separation device for the solid liquid separation zone is a rotary pressure drum filter.

The temperature of cooled crude carboxylic acid slurry steam 210 which is routed to the solid-liquid separation zone 300 can range from 35° C. to 210 °C, 55 °C to 120 °C, and is preferably from 75 °C to 95 °C. Wash solvent stream 320 comprises a liquid suitable for displacing and washing mother liquor from the solids. In one embodiment, a suitable wash solvent comprises acetic acid. In another embodiment, a suitable wash solvent comprises acetic acid and water. In yet another embodiment, a suitable wash solvent comprises water and can be 100% water. The temperature of the wash solvent can range from 20 °C to 160 °C, 40 °C to 110 °C, and preferably from 50 °C to 90 °C.

The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3. After solids are washed in the solid liquid separation zone, they are dewatered. Dewatering involves reducing the mass of moisture present with the solids to less than 30% by weight, less than 25% by weight, less than 20% by weight, and most preferably less than 15% by weight resulting in the generation of a crude carboxylic acid wet cake stream 310 comprising FDCA.

In one embodiment, dewatering is accomplished in a filter by passing a stream comprising gas through the solids to displace free liquid after the solids have been washed with a wash solvent. In an embodiment, dewatering of the wet cake solids in solid-liquid separation zone 300 can be implemented before washing and after washing the wet cake solids in zone 300 to minimize the amount of oxidizer solvent present in the wash liquor stream 340. In another embodiment, dewatering is achieved by centrifugal forces in a perforated bowl or solid bowl centrifuge.

The mother liquor steam 330 generated in solid-liquid separation zone 300 comprises oxidation solvent, catalyst, and impurities. From 5 wt % to 95 wt %, from 30 wt % to 90 wt %, and most preferably from 40 wt % to 80 wt % of mother liquor present in the crude carboxylic acid slurry 110 is isolated in solid-liquid separation zone 300 to generate mother liquor stream 330 resulting in dissolved matter comprising impurities present in mother liquor stream 330 not going forward in the process.

In one embodiment, a portion of mother liquor stream 330 is routed to a mother liquor purge zone 700, wherein a portion is at least 5 weight %, at least 25 weight %, at least 45 weight %, at least 55 weight % at least 75 weight %, or at least 90 weight %. In another embodiment, at least a portion of the mother liquor stream 330 is routed back to the oxidation zone 100, wherein a portion is at least 5 weight %.

In yet another embodiment, at least a portion of mother liquor stream 330 is routed to a mother liquor purge zone 700 and to the oxidation zone 100 wherein a portion is at least 5 weight %. In one embodiment, the mother liquor purge zone 700 comprises an evaporative step to separate oxidation solvent from stream 330 by evaporation. Solids can be present in mother liquor stream 330 ranging from about 5 weight % to about 0.5 weight %. In yet another embodiment, any portion of mother liquor stream 330 routed to a mother liquor purge zone is first subjected to a solid liquid separation device to control solids present in stream 330 to less than 1 wt %, less than 0.5 wt %, less than 0.3 wt %, or less than 0.1% by weight. Suitable solid liquid separation equipment comprise a disc stack centrifuge and batch pressure filtration solid liquid separation devices. A preferred solid liquid separation device for this application comprises a batch candle filter.

Wash liquor stream 340 is generated in the solid-liquid separation zone 300 and comprises a portion of the mother liquor present in stream 210 and wash solvent wherein the ratio of mother liquor mass to wash solvent mass is less than 3 and preferably less than 2. In an embodiment, at least a portion of wash liquor stream 340 is routed to oxidation zone 100 wherein a portion is at least 5 weight %. In an embodiment, at least a portion of wash liquor stream is routed to mother liquor purge zone 700 wherein a portion is at least 5 weight %. In another embodiment, at least a portion of wash liquor stream 340 is routed to oxidation zone 100 and mother liquor purge zone 700 wherein a portion is at least 5 weight %.

In another embodiment, at least a portion of the crude carboxylic acid slurry stream 110 up to 100 weight % is routed directly to the solid-liquid separation zone 300, thus this portion will bypass the cooling zone 200. In this embodiment, feed to the solid-liquid separation zone 300 comprises at least a portion of the crude carboxylic acid slurry stream 110 and wash solvent stream 320 to generate a crude carboxylic acid wet cake stream 310 comprising FDCA. Solids in the feed slurry are isolated, washed, and dewatered in solid-liquid separation zone 300. These functions may be accomplished in a single solid-liquid separation device or multiple solid-liquid separation devices. The solid-liquid separation zone comprises at least one solid-liquid separation device capable of separating solids and liquids, washing solids with a wash solvent stream 320, and reducing the % moisture in the washed solids to less than 30 weight %, less than 20 weight %, less than 15 weight %, and preferably less than 10 weight %. Equipment suitable for the solid liquid separation zone can typically be at least one of the following types of devices: centrifuge, cyclone, rotary drum filter, belt filter, pressure leaf filter, candle filter, and the like. The preferred solid liquid separation device for the solid liquid separation zone 300 is a continuous rotary pressure drum filter. The temperature of the crude carboxylic acid slurry stream, which is routed to the solid-liquid separation zone 300 can range from 40 °C to 210 °C, 60 °C to 170 °C, ° C. and is preferably from 80 °C to 160 °C. The wash stream 320 comprises a liquid suitable for displacing and washing mother liquor from the solids. In one embodiment, a suitable wash solvent comprises acetic acid and water. In another embodiment, a suitable wash solvent comprises water up to 100% water. The temperature of the wash solvent can range from 20 °C to 180 °C, 40 °C and 150 °C, and preferably from 50 °C to 130 °C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

After solids are washed in the solid liquid separation zone, they are dewatered. Dewatering involves reducing the mass of moisture present with the solids to less than 30% by weight, less than 25% by weight, less than 20% by weight, and most preferably less than 15% by weight resulting in the generation of a crude carboxylic acid wet cake stream 310. In one embodiment, dewatering is accomplished in a filter by passing a gas stream through the solids to displace free liquid after the solids have been washed with a wash solvent. In another embodiment, the dewatering of the wet cake in solid-liquid separation zone 300 can be implemented before washing and after washing the solids in zone 300 to minimize the amount of oxidizer solvent present in the wash liquor stream 340 by any method known in the art. In yet another embodiment, dewatering is achieved by centrifugal forces in a perforated bowl or solid bowl centrifuge.

Mother liquor steam 330 generated in the solid-liquid separation zone 300 comprising oxidation solvent, catalyst, and impurities. From 5 wt % to 95 wt %, from 30 wt % to 90 wt %, and most preferably from 40 wt % to 80 wt % of mother liquor present in the crude carboxylic acid slurry stream 110 is isolated in solid-liquid separation zone 300 to generate mother liquor stream 330 resulting in dissolved matter comprising impurities present in mother liquor stream 330 not going forward in the process. In one embodiment, a portion of mother liquor stream 330 is routed to a mother liquor purge zone 700, wherein a portion is at least 5 weight %, at least 25 weight %, at least 45 weight %, at least 55 weight % at least 75 weight %, or at least 90 weight %. In another embodiment, at least a portion is routed back to the oxidation zone 100, wherein a portion is at least 5 weight %. In yet another embodiment, at least a portion of mother liquor stream 330 is routed to a mother liquor purge zone and to the oxidation zone 100 wherein a portion is at least 5 weight %. In one embodiment, mother liquor purge zone 700 comprises an evaporative step to separate oxidation solvent from stream 330 by evaporation.

Wash liquor stream 340 is generated in the solid-liquid separation zone 300 and comprises a portion of the mother liquor present in stream 210 and wash solvent wherein the ratio of mother liquor mass to wash solvent mass is less than 3 and preferably less than 2. In an embodiment, at least a portion of wash liquor stream 340 is routed to oxidation zone 100 wherein a portion is at least 5 weight %. In an embodiment, at least a portion of wash liquor stream 340 is routed to mother liquor purge zone 700 wherein a portion is at least 5 weight %. In another embodiment, at least a portion of wash liquor stream is routed to oxidation zone 100 and mother liquor purge zone 700 wherein a portion is at least 5 weight %.

Mother liquor stream 330 comprises oxidation solvent, catalyst, soluble intermediates, and soluble impurities. It is desirable to recycle directly or indirectly at least a portion of the catalyst and oxidation solvent present in mother liquor stream 330 back to oxidation zone 100 wherein a portion is at least 5% by weight, at least 25%, at least 45%, at least 65%, at least 85%, or at least 95%. Direct recycling at least a portion of the catalyst and oxidation solvent present in mother liquor stream 330 comprises directly routing a portion of stream 330 to oxidizer zone 100. Indirect recycling at least a portion of the catalyst and oxidation solvent present in mother liquor stream 330 to oxidation zone 100 comprises routing at least a portion of stream 330 to at least one intermediate zone wherein stream 330 is treated to generate a stream or multiple streams comprising oxidation solvent and or catalyst that are routed to oxidation zone 100.

Step (d) comprises separating components of mother liquor stream 330 in mother liquor purge zone 700 for recycle to the process while also isolating those components not to be recycled comprising impurities. Impurities in stream 330 can originate from one or multiple sources. In an embodiment of the invention, impurities in stream 330 comprise impurities introduced into the process by feeding streams to oxidation zone 100 that comprise impurities. Mother liquor impurities comprise at least one impurity selected from the following group: 2,5-diformylfuran in an amount ranging from about 5 ppm to 800 ppm, 20 ppm to about 1500 ppm, 100 ppm to about 5000 ppm, 150 ppm to about 2.0 wt %; levulinic acid in an amount ranging from about 5 ppm to 800 ppm, 20 ppm to about 1500 ppm, 100 ppm to about 5000 ppm, 150 ppm to about 2.0 wt %; succinic acid in an amount ranging from about 5 ppm to 800 ppm, 20 ppm to about 1500 ppm, 100 ppm to about 5000 ppm, 150 ppm to about 2.0 wt %; acetoxy acetic acid in an amount ranging from about 5 ppm to 800 ppm, 20 ppm to about 1500 ppm, 100 ppm to about 5000 ppm, 150 ppm to about 2.0 wt %

An impurity is defined as any molecule not required for the proper operation of oxidation zone 100. For example, oxidation solvent, a catalyst system, a gas comprising oxygen, and oxidizable raw material comprising at least one compound selected from the group of formula: 5-(hydroxymethyl)furfural (5-HMF), 5-(chloromethyl)furfural (5-CMF), 2,5-dimethylfuran (2,5-DMF), 5-HMF esters (5-R(CO)$OCH_2$-furfural where R=alkyl, cycloalkyl and aryl), 5-HMF ethers (5-R'$OCH_2$-furfural, where R'=alkyl, cycloalkyl and aryl), 5-alkyl furfurals (5-R"-furfural, where R"=alkyl, cycloalkyl and aryl), alkylcarboxylate of methyfuran (5-R'''O(CO)-methylfuran, where R'''=alkyl, cycloalkyl), alkylcarboxylate of alkoxyfuran (5-R''''O(CO)—OR'''''furan, where R''''=alkyl, cycloalkyl and aryl and R'''''=alkyl, cycloalkyl and aryl), mixed feed-stocks of 5-HMF and 5-HMF esters and mixed feed-stocks of 5-HMF and 5-HMF ethers, mixed feed-stocks of 5-HMF and 5-alkyl furfurals, mixed feed-stocks of 5-HMF and 5-CMF, mixed feed-stocks of 5-HMF and 2,5-DMF, mixed feed-stocks of 5-HMF and alkylcarboxylate of methyfuran, mixed feed-stocks of 5-HMF and alkylcarboxylate of alkoxyfuran are molecules required for the proper operation of oxidation zone 100 and are not considered impurities. Also, chemical intermediates formed in oxidation zone 100 that lead to or contribute to chemical reactions that lead to desired products are not considered impurities. Oxidation by-products that do not lead to desired products are defined as impurities. Impurities may enter oxidation zone 100 through recycle streams routed to the oxidation zone 100 or by impure raw material streams fed to oxidation zone 100.

In one embodiment, it is desirable to isolate a portion of the impurities from oxidizer mother liquor stream 330 and purge or remove them from the process as purge stream 751. In an embodiment of the invention, from 5 to 100% by weight, of mother liquor stream 330 generated in solid-liquid separation zone 300 is routed to mother liquor purge zone 700 wherein a portion of the impurities present in stream 330 are isolated and exit the process as purge stream 751. The portion of stream 330 going to the mother liquor purge zone 700 can be 5% by weight or greater, 25% by weight or greater, 45% by weight or greater, 65% by weight or greater, 85% by weight or greater, or 95% by weight or greater. Recycle oxidation solvent stream 711 comprises oxidation solvent isolated from stream 330 and can be recycled to the process. The raffinate stream 742 comprises oxidation catalyst isolated from stream 330 which can optionally be recycled to the process. In one embodiment, the raffinate stream 742 is recycled to oxidation zone 100 and contains greater than 30 wt %, greater than 50 wt %, greater than 80 wt %, or greater than 90 wt % of the catalyst that entered the mother liquor purge zone 700 in stream 330. In another embodiment, at least a portion of mother liquor stream 330 is routed directly to oxidation zone 100 without first being treated in mother liquor purge zone 700. In one embodiment, mother liquor purge zone 700 comprises an evaporative step to separate oxidation solvent from stream 330 by evaporation.

One embodiment of mother liquor purge zone 700 comprises routing at least a portion of oxidizer mother liquor stream 330 to solvent recovery zone 710 to generate a recycle oxidation solvent stream 711 comprising oxidation solvent and an impurity rich waste stream 712 comprising oxidation by products and catalyst. Any technology known in the art capable of separating a volatile solvent from stream 330 may be used. Examples of suitable unit operations include, but are not limited to, batch and continuous evaporation equipment operating above atmospheric pressure, at atmospheric pressure, or under vacuum. A single or multiple evaporative steps may be used. In an embodiment of the invention, sufficient oxidation solvent is evaporated from stream 330 to result in stream 712 being present as a slurry having a weight percent solids greater than 10 weight percent, 20 weight percent, 30 weight percent, 40 weight percent, or 50 weight percent. At least a portion of impurity rich stream 712 can be routed to catalyst recovery zone 760 to generate catalyst rich stream 761. Examples of suitable unit operations for catalyst recovery zone 760 include, but are not limited to, incineration or burning of the stream to recover noncombustible metal catalyst in stream 761.

Another embodiment of mother liquor purge zone 700 comprises routing at least a portion of mother liquor stream 330 to solvent recovery zone 710 to generate a recycle oxidation solvent stream 711 comprising oxidation solvent and an impurity rich waste stream 712 comprising oxidation by products and catalyst. Any technology known in the art capable of separating a volatile solvent from stream 330 may be used. Examples of suitable unit operations include but are not limited to batch and continuous evaporation equipment operating above atmospheric pressure, at atmospheric pressure, or under vacuum. A single or multiple evaporative steps may be used. Sufficient oxidation solvent is evaporated from stream 330 to result in impurity rich waste stream 712 being present as slurry with weight % solids greater than 5 weight percent, 10 weight percent, 20 weight percent, and 30 weight percent. At least a portion of the impurity rich waste stream 712 is routed to a solid liquid separation zone 720 to generate a purge mother liquor stream 723 and a wet cake stream 722 comprising impurities. In another embodiment of the invention, all of stream 712 is routed to the solid liquid separation zone 720. Stream 722 may be removed from the process as a waste stream. Wash stream 721 may also be routed to solid-liquid separation zone 720 which will result in wash liquor being present in stream 723. It should be noted that zone 720 is a separate and different zone from zone 300.

Any technology known in the art capable of separating solids from slurry may be used. Examples of suitable unit operations include, but are not limited to, batch or continuous filters, batch or continuous centrifuges, filter press, vacuum belt filter, vacuum drum filter, continuous pressure drum filter, candle filters, leaf filters, disc centrifuges, decanter centrifuges, basket centrifuges, and the like. A continuous pressure drum filter is a preferred device for solid-liquid separation zone 720.

Purge mother liquor stream 723 comprising catalyst and impurities, and stream 731 comprising a catalyst solvent are routed to mix zone 731 to allow sufficient mixing to generate extraction feed stream 732. In one embodiment, stream 731 comprises water. Mixing is allowed to occur for at least 30 seconds, 5 minutes, 15 minutes, 30 minutes, or 1 hour. Any technology know in the art may be used for this mixing operation including inline static mixers, continuous stirred tank, mixers, high shear in line mechanical mixers and the like.

Extraction feed stream 732, recycle extraction solvent stream 752, and fresh extraction solvent stream 753 are routed to liquid-liquid extraction zone 740 to generate an extract stream 741 comprising impurities and extract solvent, and a raffinate stream 742 comprising catalyst solvent and oxidation catalyst that can be recycled directly or indirectly to the oxidation zone 100. Liquid-liquid extraction zone 740 may be accomplished in a single or multiple extraction units. The extraction units can be batch and or continuous. An example of suitable equipment for extraction zone 740 includes multiple single stage extraction units. Another example of suitable equipment for extraction zone 740 is a single multi stage liquid-liquid continuous extraction column. Extract stream 741 is routed to distillation zone 750 where extraction solvent is isolated by evaporation and condensation to generate recycle extract solvent stream 752. The purge stream 751 is also generated and can be removed from the process as a waste purge stream. Batch or continuous distillation may be used in distillation zone 750.

In another embodiment, the source for oxidizer mother liquor stream 330 feeding mother liquor purge zone 700 may originate from any mother liquor stream comprising oxidation solvent, oxidation catalyst, and impurities generated in process to make furan-2,5-dicarboxylic acid (FDCA). For example, a solvent swap zone downstream of oxidation zone 100 that isolates at least a portion of the FDCA oxidation solvent from stream 110 can be a source for stream 330. Suitable equipment for a solvent swap zone comprises solid-liquid separation devices including centrifuges and filters. Examples of suitable equipment for the solvent swap include, but is not limited to, a disc stack centrifuge or a continuous pressure drum filter.

EXAMPLES

Analytical Techniques

Liquid Chromatographic Method for Sample Analysis

Samples were analyzed with an Agilent 1260 LC unit having a quaternary pump, an autosampler (3 uL injection), a thermostated column compartment (35 °C), and a diode array UV/vis detector (280 nm). The chromatograph was fitted with a 150 mm×4.6 mm Thermo Aquasil C18 column packed with 3-micron particles. The solvent flow program used is shown in the table below. Channel A was 0.1% phosphoric acid in water, channel B was acetonitrile, and channel C was tetrahydrofuran (THF).

| Time (min) | % A | % B | % C | Flowrate (mL/min) |
|---|---|---|---|---|
| Initial | 95.0 | 0.0 | 5.0 | 1.50 |
| 6 | 95 | 0 | 5.0 | 1.50 |
| 6.1 | 65 | 30 | 5.0 | 1.50 |

-continued

| Time (min) | % A | % B | % C | Flowrate (mL/min) |
|---|---|---|---|---|
| 9 | 65 | 30 | 5.0 | 1.50 |
| 10.1 | 15 | 80 | 5.0 | 1.50 |
| 12 | 15 | 80 | 5.0 | 1.50 |
| 12.1 | 95 | 0 | 5.0 | 1.50 |
| 17 | 95 | 0 | 5.0 | 1.50 |

EZChrom elite was used for control of the HPLC and for data processing. A 5-point linear calibration was used in the (approximate) range of 0.25 to 100 ppm for FFCA, FDCA, MCFC, MMFC, and MFFC. Solid samples were prepared by dissolving ~0.05 g (weighed accurately to 0.0001 g) in 10 mL of 50:50 DMF/THF so that ppm levels of FFCA and MFFC could be detected. For purity analysis, the samples were further diluted by pipetting a 100 μL sample into a 10 mL volumetric flask and diluted to volume with 50:50 DMF/THF. Sonication was used to ensure complete dissolution of the sample in the solvent. For liquid samples, 0.1 g of sample was weight out and diluted to 10 mL with 50:50 DMF/THF. A small portion of the prepared sample was transferred to an auto sampler vial for injection onto the LC.

Color Measurement

1) Assembled the Carver Press die as instructed in the directions—placed the die on the base and placed the bottom 40-mm cylinder polished side face-up.
2) Placed a 40-mm plastic cup (Chemplex Plasticup, 39.7×6.4 mm) into the die.
3) Filled the cup with the sample to be analyzed. The exact amount of sample added is not important.
4) Placed the top 40-mm cylinder polished side face-down on the sample.
5) Inserted the plunger into the die. No "tilt" should be exhibited in the assembled die.
6) Placed the die into the Carver Press, making sure that it is near the center of the lower platen. Closed the safety door.
7) Raised the die until the upper platen made contact with the plunger. Applied >10,000 lbs. pressure. Then allowed the die to remain under pressure for approximately 30 seconds (exact time not critical).
8) Released the pressure and lowered the lower platen holding the die.
9) Disassembled the die and remove the cup. Placed the cup into a labeled plastic bag (Nasco Whirl-Pak 4 oz).
10) Using a HunterLab UltraScan Pro colorimeter, created the following method (Hunterlab EasyMatchQC software, version 3.6.2 or later):
    Mode: RSIN-LAV (Reflectance Specular Included)
    Area View: 0.78 in.
    UV Filter Position: Nominal
    Measurements:
        CIE L* a* b*
        CIE X Y Z
11) Standardized the instrument as prompted by the software using the light trap accessory and the certified white tile accessory pressed against the reflectance port.
12) Ran a green tile standard using the certified white tile and compared the CIE X, Y, and Z values obtained against the certified values of the tile. The values obtained should be ±0.15 units on each scale of the stated values.

13) Analyzed the sample in the bag by pressing it against the reflectance port and obtaining the spectrum and L*, a*, b* values. Obtained duplicate readings and average the values for reporting.

EXAMPLES

Air Oxidation of Methyl 5-Methylfuran-2-Carboxylate (MMFC)

The air oxidation of MMFC in an acetic acid solvent using a catalyst system containing cobalt, manganese, and bromine was carried out according to the general procedures below. The reaction is shown in equation 1:

eq 1

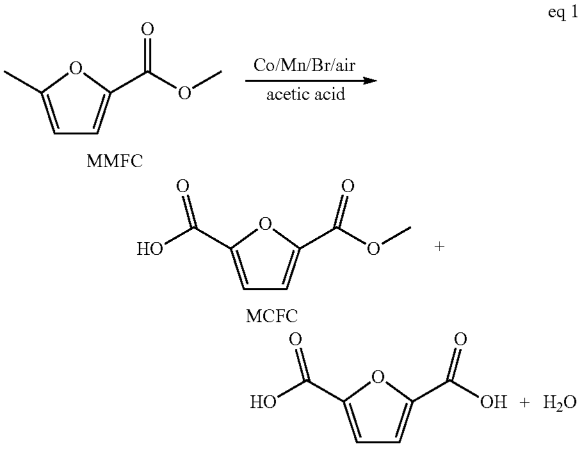

MMFC

MCFC

+ $H_2O$

FDCA

General Procedures

Glacial acetic acid (125.7 g) and the catalyst components in the amounts described in Table 1 were transferred to a 300-mL titanium autoclave equipped with a high-pressure condenser, a baffle, and an Isco pump. Cobalt, manganese, and ionic bromine were provided as cobalt (II) acetate tetrahydrate, manganese (II) acetate, and aqueous hydrobromic acid (48.7 wt % in water), respectively.

The autoclave was pressurized with approximately 50 psig of nitrogen, and the homogeneous mixture was heated to the desired temperature in a closed system (i.e., with no gas flow) with stirring.

At the desired reaction temperature, an air flow of 1500 sccm was introduced at the bottom of the solution, and the reaction pressure was adjusted to the desired level. Liquid MMFC was fed at a rate of 0.20 mL/min via a high-pressure Isco pump (this is t=0 for the reaction time).

After 30 seconds from the start of the substrate feeding, 1.0 g of peracetic acid (32 wt % in acetic acid) in 5.0 g of acetic acid was introduced using a blow-case to start the reaction.

The feed was stopped after 1 h, and the reaction continued for an additional hour at the same conditions of air flow, temperature, and pressure.

After the reaction time was completed, the air flow was stopped, and the autoclave was cooled to room temperature and depressurized to obtain a heterogeneous mixture.

The heterogeneous mixture was filtered to isolate a white product. The mass of the filtrate was recorded. The white product was washed with 60 mL of acetic acid two times. The washed white product was oven dried at 110 °C under vacuum overnight, and then weighed. The solid product, the filtrate, and the acetic acid washes were analyzed by Liquid Chromatography.

The Off-gas was analyzed for CO and $CO_2$ by ND-1R (ABB, Advanced Optima) and $O_2$ by a paramagnetism detection system (Servomex, 1440 Model).

The results are reported in Table 1. The LC chromatogram of the white, solid product from Example 3 is shown in the Figure.

TABLE 1

Results from Semi-Batch Oxidation of MMFC at Different Conditions

| | Example No. | | | | |
|---|---|---|---|---|---|
| | 1 | 2 | 3 | 4 | 5 |
| Temp. (°C) | 110 | 132 | 132 | 155 | 170 |
| Pressure (psig) | 130 | 130 | 130 | 130 | 130 |
| $Co(OAc)_2 4H_2O$ (g) | 1.56 | 1.56 | 1.56 | 1.56 | 1.57 |
| $Mn(OAc)_2$ (g) | 0.054 | 0.060 | 1.081 | 0.050 | 0.050 |
| Aq. HBr[a] (g) | 0.92 | 0.93 | 0.91 | 0.93 | 0.92 |
| MMFC[b] (g) | 13.1 | 13.1 | 13.1 | 13.1 | 13.1 |
| MMFC Conversion (%) | 99.39 | 99.94 | 99.93 | 99.95 | 99.98 |
| MCFC Yield[c] (%) | 77.6 | 84.7 | 77.6 | 75.62 | 52.5 |
| FDCA Yield[c] (%) | 0.2 | 1.7 | 1.5 | 6.6 | 15.2 |
| Solid Product Composition | | | | | |
| MCFC (wt %) | 99.39 | 98.44 | 97.56 | 94.65 | 72.63 |

TABLE 1-continued

Results from Semi-Batch Oxidation of MMFC at Different Conditions

| | Example No. | | | | |
|---|---|---|---|---|---|
| | 1 | 2 | 3 | 4 | 5 |
| FDCA (wt %) | 0.036 | 1.34 | 1.15 | 5.29 | 27.26 |
| MFFC (ppmw) | 2504.6 | 95.7 | 379.8 | 123.3 | 246.6 |
| FFCA (ppmw) | 5.4 | 1.71 | 318.6 | 0 | 0.002 |
| b* | 0.34 | −0.11 | 0.62 | 0.15 | −0.59 |
| CO (total mol) | 0.008 | 0.008 | 0.011 | 0.012 | 0.01 |
| $CO_2$ (total mol) | 0.06 | 0.051 | 0.008 | 0.065 | 0.107 |
| $CO_x$ (total mol) | 0.000283 | 0.000246 | 0.000079 | 0.000321 | 0.000488 |

[a]= 48.7 wt % in water;
[b]= 97.8 wt % purity;
[c]= in solid, filtrate, and AA washes As seen from Table 1, the oxidation reaction mainly formed MCFC, instead of FDGA. This reaction produces water as a byproduct, but surprisingly, under certain conditions, hydrolysis of the methyl ester bond by the water to make FDCA was very minimal.

It is also worth noting from Table 1 that it is possible to produce a high-purity product with an FFCA level of only 1.71 ppmw, an MFFC level of only 95.7 ppmw, and a b* level of −0.11 in one (main) oxidation step. FFCA and MFFC are known chain terminators in a polymerization process. At such low levels of impurities and color, this product can be used directly to make a polymer without further purification. That a polymer grade monomer can be made with no additional purification steps has significant economic advantages.

The invention has been described in detail with particular reference to specific embodiments thereof, but it will be understood that variations and modifications can be made within the spirit and scope of the invention.

We claim:

1. A purge mother liquor composition produced by the process for preparing a compound of the structural formula (I):

(I)

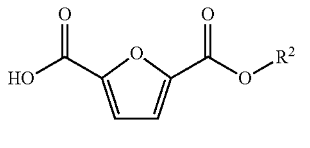

the process comprising contacting a compound of the structural formula (II):

(II)

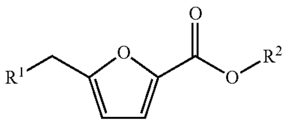

with an oxidizing agent in the presence of an oxidation catalyst and a solvent, wherein:

the oxidation catalyst comprises cobalt, manganese, and bromine;

the solvent comprises a monocarboxylic acid having 2 to 6 carbon atoms;

$R^1$ is hydrogen, $R^3O$—, or $R^3C(O)O$—;

$R^2$ is an alkyl group having 1 to 6 carbon atoms; and $R^3$ is hydrogen or an alkyl group having 1 to 6 carbon atoms;

wherein $R^3$ is hydrogen or an alkyl group having 1 to 3 carbon atoms, and wherein $R^2$ is a methyl group and routing said mother liquor stream in a solvent recovery zone to form a recycle oxidation solvent stream and an impurity rich waste stream; and routing a portion of said impurity rich waste stream to a solid-liquid separation zone to form a said purge mother liquor stream, wherein a portion of said solvent is recycled from the purge process to the oxidation reactor.

2. The process according to claim 1, wherein the oxidizing agent is oxygen.

3. An impurity rich stream produced by the process of claim 1.

4. The process according to claim 1, wherein the contacting step is conducted at a temperature of 100 °C to 180 °C.

5. The process according to claim 1, wherein the oxidizing agent is oxygen, air, or other oxygen-containing gas.

6. The process according to claim 1, wherein the contacting step is conducted at a pressure of 50 psig to 1000 psig.

7. The process according to claim 1, wherein the solvent comprises acetic acid.

8. The process according to claim 1, wherein the bromine is derived from hydrobromic acid or sodium bromide.

9. The process according to claim 1, wherein the weight ratio of Co: Mn ranges from 0.1:1 to 100:1.

10. The process according to claim 1, wherein the weight ratio of Co: Mn ranges from 20:1 to 100:1.

11. The process according to claim 1, wherein the yield of compound (I) is at least 70%.

12. The process according to claim 1, wherein the yield of furan-2,5-dicarboxylic acid (FDCA) is less than 20%.

13. The process according to claim 1, which produces a dried, solid product comprising at least 70 wt % of the compound (I), based on the total weight of the product.

14. The process according to claim 1, which produces a dried, solid product comprising at least 99 wt % of the compound (I), based on the total weight of the product.

15. The process according to claim 14, wherein the dried, solid product comprises less than 30 wt % of furan-2,5-dicarboxylic acid (FDCA), based on the total weight of the product.

16. The process according to claim 13, wherein the dried, solid product comprises less than 500 ppmw of 5-formylfuran-2-carboxylic acid (FFCA), based on the total weight of the product.

17. The process according to claim 13, wherein the dried, solid product comprises less than 1000 ppmw of alkyl 5-formylfuran-2-carboxylate (AFFC), based on the total weight of the product.

18. The process according to claim 13, wherein the dried, solid product has a b* value of less than 4.

19. The process according to claim 13, wherein the dried, solid product has a b* value from −1 to +1.

20. The process according to claim 13, wherein the dried, solid product is obtained without performing a secondary oxidation step, a hydrogenation step, or a treatment step with an oxidizer.

* * * * *